US007465755B2

(12) United States Patent
Araldi et al.

(10) Patent No.: US 7,465,755 B2
(45) Date of Patent: Dec. 16, 2008

(54) HYDRAZIDE DERIVATIVES AS PROSTAGLANDIN RECEPTORS MODULATORS

(75) Inventors: Gian Luca Araldi, Sedauket, NY (US); Yihua Liao, Westwood, MA (US); Nadia Brugger, Cambridge, MA (US)

(73) Assignee: Laboratoires Serono SA, Vaud (CH)

( * ) Notice: Subject to any disclaimer, the term of this patent is extended or adjusted under 35 U.S.C. 154(b) by 66 days.

(21) Appl. No.: 10/564,974

(22) PCT Filed: Jul. 16, 2004

(86) PCT No.: PCT/EP2004/051531

§ 371 (c)(1),
(2), (4) Date: Jul. 11, 2006

(87) PCT Pub. No.: WO2005/012232

PCT Pub. Date: Feb. 10, 2005

(65) Prior Publication Data

US 2007/0185191 A1    Aug. 9, 2007

Related U.S. Application Data

(60) Provisional application No. 60/488,614, filed on Jul. 18, 2003.

(51) Int. Cl.
*A61K 31/24* (2006.01)
*C07D 205/02* (2006.01)
(52) U.S. Cl. .............................. 514/534; 560/22; 560/23
(58) Field of Classification Search ................. 514/534; 560/22, 23
See application file for complete search history.

(56) References Cited

FOREIGN PATENT DOCUMENTS

| EP | 1 114 816 | 7/2001 |
|---|---|---|
| WO | 99 02164 | 1/1999 |
| WO | 99 33794 | 7/1999 |
| WO | 00 03980 | 1/2000 |
| WO | 01 46140 | 6/2001 |
| WO | 02 24647 | 3/2002 |
| WO | 02 42268 | 5/2002 |

OTHER PUBLICATIONS

Abramovitz et al. "The utilization of recombinant prostanoid receptors to determine the affinities and selectivities of prostaglandins and related analogs", Biochimica et Biophysica Acta, vol. 1483, pp. 285-293 2000.
Benoit et al. "Latest discoveries in prostaglandin receptor modulators", Expert. Opin. Ther. Patents, vol. 12, No. 8, pp. 1225-1235 2002.
Choung et al. "Role of EP2 Receptors and cAMP in Prostaglandin E2 Regulated Expression of Type I Collagen alpha1, Lysyl Oxidase, and Cyclooxygenase-1 Genes in Human Embryo Lung Fibroblasts", Journal of Cellular Biochemistry, vol. 71, pp. 254-263 1998.

Coleman et al. "Prostanoids and their Receptors", In Comprehensive Medicinal Chemistry, The rational Design, Machanistic Study and Therapeutic Application of Chemical Compounds, vol. 3, pp. 643-714 1989.
Coleman et al. "VIII. International Union of Pharmacology Classification of Prostanoid Receptors: Properties, Distribution, and Structure of the Receptors and Their Subtypes", Pharmacological Reviews, vol. 46, No. 2, pp. 205-229 1994.
Fleisch et al. "LY171883, 1-<2-Hydroxy-3-Propyl-4-<4-(1H-Tetrazol-5-yl) Butoxy>Phenyl>Ethanone, an Orally Active Leukotriene D4 Antagonist", Journal of Pharmacology and Experimental Therapeutics, vol. 233 No. 1, pp. 148-157 1985.
Formica et al. "Comparative Assessment of Bone Mineral Measurements Using Dual X-ray Absorptiometry and Peripheral Quantitative Computed Tomography", Osteoporos Int, vol. 8, pp. 460-467.
Hyman et al. "Oral prostaglandin (PGE2) therapy for chronic viral hepatitis B and C", Journal of Viral Hepatitis, vol. 6, pp. 329-336 1999.
Meltzer et al. "Substituted 3-Phenyltropane Analogs of Cocaine: Synthesis, Inhibition of Binding at Cocaine Recognition Sites, and Positron Emission Tomography Imaging", J. Med. Chem. vol. 36, pp. 855-862 1993.
Miyaura, "Role of EP4 receptor in bone resorption induced by PGE", Folia Pharmacol. Jpn., vol. 117, pp. 293-297 with partial English translation 2001.
De Mico et al. J. Org. Chem., vol. 62, pp. 6974-6977 1997.
Levi et al. "Regulation of Prostanoid synthesis in microglial cells and effects of prostaglandin E2 on microglial functions", Biochemie, vol. 80, pp. 899-904 1998.
Gao et al. "Catalytic Asymmetric Epoxidation and Kinetic Resolution: Modified Procedures Including in Situ Derivatization", J. Am. Chem. Soc., vol. 109, pp. 5765-5780 1987.
Katsuki et al. "Synthesis of Saccharides and Related Polyhydroxylated Natural Products. 2. Simple Deoxyalditols", J. Org. Chem., vol. 47, pp. 1378-1380 1982.
Takayama et al. "Prostaglandin E2 Suppresses Chemokine Production in Human Macrophages through the EP4 Receptor", Journal of Biological Chemistry, vol. 277, No. 46, pp. 44147-44154.
Tsugeno et al. "Vertebral Fracture and Cortical Bone Changes in Corticosteroid-Induced Osteoporosis", Osteoporos Int, vol. 13, pp. 650-656 2002.
Ushikubi et al. "Roles of Prostanoids Revealed From Studies Using Mice Lacking Specific Prostanoid Receptors", Jpn. J. Pharmacol., vol. 83, pp. 279-285 2000.

*Primary Examiner*—Taofiq A Solola
(74) *Attorney, Agent, or Firm*—Oblon, Spivak, McClelland, Maier & Neustadt, P.C.

(57) ABSTRACT

The present invention relates to hydrazide derivatives of Formula I notably for use as pharmaceutically active compounds, as well as to pharmaceutical formulations containing such hydrazide derivatives. Said hydrazide derivatives are useful in the treatment of preterm labor, dysmenorrhea, fertility disorders, asthma, hypertension, undesired blood clotting, preelampsia, eclampsia, an eosinophil disorder, undesired bone loss, renal dysfunction, an immune deficiency disorder, ichthyosis, elevated intraocular pressure, infertility, sexual dysfunction, gastric ulcers and inflammatory disorders.

25 Claims, No Drawings

HYDRAZIDE DERIVATIVES AS PROSTAGLANDIN RECEPTORS MODULATORS

FIELD OF THE INVENTION

The present invention is directed to hydrazide derivatives, in particular for use as medicaments, as well as pharmaceutical formulations containing such hydrazide derivatives. Said hydrazide derivatives are useful in the treatment and/or prevention of asthma, hypertension, osteoporosis, sexual dysfunction, renal dysfunction (acute and chronic), immune deficiency disorder or disease, elevated intra-ocular pressure such as associated with glaucoma, ulcers, inflammatory disorders, fertility disorders and other diseases and disorders associated with the prostaglandin and receptors thereof. Preferably, the hydrazide derivatives display a modulatory, notably an agonist activity on the prostaglandin receptors, particularly prostaglandin E receptors. More preferably, said compounds are useful in the treatment and/or prevention of disease states mediated by prostaglandin EP2 and/or EP4 receptors, including asthma, fertility, osteoporosis, inflammatory and sexual disorders.

BACKGROUND OF THE INVENTION

Prostaglandins (PGs) which belong to the prostanoids family are known to have diverse biological activities such as contraction and relaxation of smooth muscle, inhibition and enhancement of neurotransmitter release, inflammation, including pain and bone metabolism (Coleman et al. 1989; EP1114816).

In particular, Prostaglandin E2 (PGE2) which is the naturally-occurring agonist of EP receptor, was found to have various roles in ovulation and fertilization, in the control of blood pressure, febrile responses, regulation of bicarbonate secretion induced by acid-stimulation in the duodenum, bone resorption, smooth muscle contraction regulation, TNF down-regulation and inhibition of microglial IL-12 secretion (Ushikubi et al., 2000; Miyaura. et al., 2001, *Nippon Yakunigaku Zasshi*, 117(4): 293-7; Benoit et al., 2002 and Levi et al., 1998 *Biochimie* 80(11):899-904).

The EP receptor has been further classified into four different receptor sub-types: EP1, EP2, EP3, and EP4 (Coleman et al. 1994).

Knock-out mice lacking each sub-type of the EP receptor gave evidence of the different roles played by these receptors (Ushikubi et al., 2000) in various mechanisms. The EP receptors are for example involved in mechanisms such as ovulation (EP2), blood pressure control (EP2), closure of ductus arteriosus (EP4), bone resorption (EP4) (Miyaura et al., 2001), erectile dysfunction (EP4) and anti-inflammatory activity (EP4) (Takayama et al., 2002).

Renal Prostaglandin E2 (PGE2) is crucial for normal renal function by dilating the glomerular microcirculation and vasa recta, applying the renal medulla and modulating salt and water transport in the distal tube.

The administration of oral PGE2 was associated with sustained loss of viral replication in 47% of chronic hepatitis B patients (Hyman et al., 1999).

As prostaglandin E2 (PGE2) is a natural ligand for all sub-types of the EP receptor, selective effects on one of the sub-types of the EP receptor is impossible to achieve with the endogenous prostaglandins.

Several prostanoid receptors and modulators of those receptors have been reported with different range of selectivity for the various receptor subtypes (Coleman et al. 1994, Abramowitz et al., 2000; Benoit et al., 2002).

Recently, EP2 agonists have been developed (U.S. Pat. No. 6,235,780 and WO 99/33794). The combination of an EP2 agonist with an EP4 agonist has been developed as combined treatment for osteoporosis (US 20010056060). EP4 selective agonists have been developed for the treatment of bone disorders (WO 02/42268 and WO 01/46140), erectile dysfunction (WO 99/02164) and other prostaglandin related disorders (WO 02/24647, US 20020004495, WO 00/03980). EP2 and EP4 antagonists have been also reported (Benoit et al., 2002).

It would be desirable to develop new compounds and methods of treatment of diseases and disorders associated with the prostaglandin family, notably EP2 and/or EP4 receptors subtypes.

SUMMARY OF THE INVENTION

It is an object of the present invention to provide substances which are suitable for the treatment and/or prevention of disorders related to prostaglandins.

It is also an object of the present invention to provide substances which are suitable for the treatment and/or prevention of respiratory disorders including asthma, emphysema and no chronic obstructive pulmonary disorder (COPD).

It is also an object of the present invention to provide substances which are suitable for the treatment and/or prevention of preterm labor or dysmenorrhea.

It is also an object of the present invention to provide substances which are suitable for the treatment and/or prevention of osteoporosis.

It is also an object of the present invention to provide substances which are suitable for the treatment and/or prevention of sexual dysfunction, including erectile dysfunction.

It is also an object of the present invention to provide substances which are suitable for the treatment and/or prevention of infertility, including ovulatory disorders.

It is also an object of the present invention to provide substances which are suitable for the treatment and/or prevention of inflammatory disorders, including Inflammatory Bowel Disease (IBD), Crohn's disease, joint inflammation and pulmonary inflammation.

It is also an object of the present invention to provide substances which are suitable for the treatment and/or prevention of ulcers, including gastric ulcers and ulcerative colitis.

It is notably an object of the present invention to provide chemical compounds which are able to agonize, the function of EP receptors, especially EP2 and/or EP4 receptors in disease states in mammals, especially in humans.

It is also an object of the present invention to provide small molecule chemical compounds for the modulation, preferably the agonization of the prostaglandin EP receptors, especially EP2 and/or EP4 receptors.

It is furthermore an object of the present invention to provide a new category of pharmaceutical formulations for the treatment and/or prevention of infertility; ovulatory disorders; respiratory disorders including asthma, emphysema and chronic obstructive pulmonary disorder (COPD); preterm labor; dysmenorrhea; osteoporosis; sexual dysfunction; inflammatory disorders, including Inflammatory Bowel Disease (IBD), Crohn's disease, joint inflammation and pulmonary inflammation; ulcers, including gastric ulcers and ulcerative colitis; and/or diseases mediated by the EP receptors, especially EP2 and/or EP4 receptors.

It is finally an object of the present invention to provide a method for the treatment and/or prevention of disorders selected from infertility; ovulatory disorders; respiratory disorders including asthma, emphysema and chronic obstructive pulmonary disorder (COPD); preterm labor; dysmenorrhea; osteoporosis; sexual dysfunction; inflammatory disorders, including Inflammatory Bowel Disease (IBD), Crohn's disease, joint inflammation and pulmonary inflammation; ulcers, including gastric ulcers and ulcerative colitis.

It is finally an object of the invention to provide a process for the preparation of compounds which are suitable for the treatment and/or prevention of disorders related to prostaglandins.

In a first aspect, the invention provides hydrazide derivatives of Formula I:

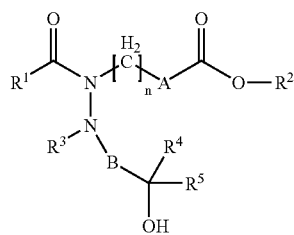

(I)

as well as its geometrical isomers, its optically active forms as enantiomers, diastereomers and mixtures of these, as well as salts thereof, wherein:

A is a divalent radical selected from optionally substituted $C_3$-$C_8$ cycloalkyl, optionally substituted heterocycloalkyl, optionally substituted aryl and optionally substituted heteroaryl;

B is a divalent radical optionally substituted $C_1$-$C_6$ alkylene, optionally substituted $C_2$-$C_6$ alkenylene, and optionally substituted $C_2$-$C_6$ alkynylene;

$R^1$ is selected from optionally substituted $C_1$-$C_6$ alkyl, optionally substituted $C_2$-$C_6$ alkenyl, optionally substituted $C_2$-$C_6$ alkynyl, optionally substituted $C_3$-$C_8$ cycloalkyl, optionally substituted heterocycloalkyl, optionally substituted $C_3$-$C_8$ cycloalkyl $C_1$-$C_6$ alkyl, optionally substituted aryl $C_1$-$C_6$ alkyl, optionally substituted heteroaryl $C_1$-$C_6$ alkyl, optionally substituted aryl and optionally substituted heteroaryl;

$R^2$ and $R^3$ are independently selected from hydrogen, optionally substituted $C_1$-$C_6$ alkyl, optionally substituted $C_2$-$C_6$ alkenyl and optionally substituted $C_2$-$C_6$ alkynyl;

$R^4$ is selected from hydrogen and optionally substituted $C_1$-$C_6$ alkyl;

$R^5$ is selected from hydrogen, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ heteroalkyl, optionally substituted $C_1$-$C_6$ heteroalkyl, optionally substituted $C_3$-$C_8$ cycloalkyl, optionally substituted $C_3$-$C_8$ cycloalkyl $C_1$-$C_6$ alkyl, optionally substituted aryl $C_1$-$C_6$ alkyl, optionally substituted heteroaryl $C_1$-$C_6$ alkyl, optionally substituted aryl and optionally substituted heteroaryl;

n is an integer selected from 1, 2, 3, 4, 5 and 6.

In a second aspect, the present invention provides hydrazide derivatives of Formula I for use as a medicament.

In a third aspect, the invention provides a pharmaceutical composition comprising a compound of Formula I, together with a pharmaceutically acceptable excipient or carrier.

In a fourth aspect, the invention provides a use of a compound of Formula I for the preparation of a pharmaceutical composition useful for a variety of therapies, including alleviating, preventing and/or treating pre-term labor; cervical ripening; dysmenorrhea; respiratory disorders including asthma, emphysema and chronic obstructive pulmonary disorder (COPD); hypertension; undesired blood clotting; preeclampsia or eclampsia, an eosinophil disorder; osteoporosis and other destructive bone disease or disorder; renal dysfunction (acute and chronic); immune deficiency disorder or disease; dry eye; skin disorders such as ichthyosis; elevated intra-ocular pressure such as associated with glaucoma; ulcers; sexual dysfunction; including erectile dysfunction, fertility disorders; including ovulatory disorders; inflammatory disorders and other diseases and disorders associated with the prostaglandin family of compounds and receptors thereof.

In a fifth aspect, the invention provides a method for treating a patient suffering from pre-term labor; cervical ripening; dysmenorrhea; respiratory disorders including asthma, emphysema and chronic obstructive pulmonary disorder (COPD); hypertension; undesired blood clotting; preeclampsia or eclampsia; an eosinophil disorder; osteoporosis and other destructive bone disease or disorder, renal dysfunction (acute and chronic); immune deficiency disorder or disease; dry eye; skin disorders such as ichthyosis; elevated intra-ocular pressure such as associated with glaucoma; ulcers; sexual dysfunction; including erectile dysfunction; fertility disorders; including ovulatory disorders; inflammatory disorders. The method comprises administering a compound according to Formula I.

In a sixth aspect, the invention provides a method for treating a disease associated with prostaglandins. The method comprises administering a compound according to Formula I.

In a seventh aspect, the invention provides a process for preparing a hydrazide of Formula I, wherein $R^4$ is H, comprising the step of a reductive amination of a hydrazide of Formula II with a compound of Formula III in presence of a reducing agent:

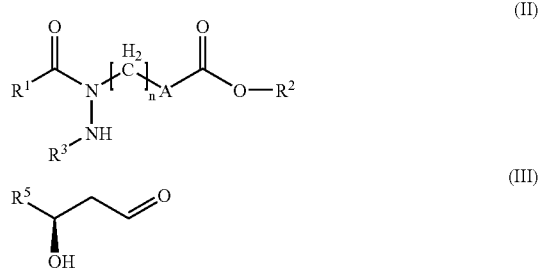

wherein A, $R^1$, $R^2$, $R^3$ and n are as defined above; $R^5$ is —$CH^2$—$R^6$ wherein $R^6$ is selected from optionally substituted $C_1$-$C_5$ alkyl, optionally substituted $C_2$-$C_5$ alkenyl, optionally substituted $C_2$-$C_5$ alkynyl, optionally substituted $C_1$-$C_5$ heteroalkyl, optionally substituted $C_1$-$C_5$ alkyl $C_1$-$C_5$ alkyl, optionally substituted aryl $C_1$-$C_5$ alkyl and optionally substituted heteroaryl $C_1$-$C_5$ alkyl.

In a eighth aspect, the invention provides a process for preparing a hydrazide Formula I, wherein $R^4$ is H, comprising the step of a reduction of a compound of Formula IV:

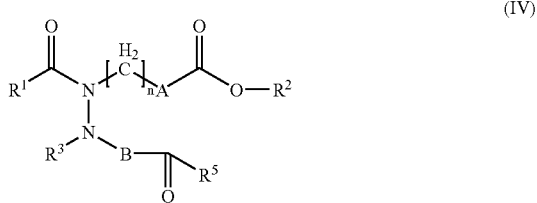

wherein A, B, $R^1$, $R^2$, $R^3$, $R^5$ and n are as defined above.

In a ninth aspect, the invention provides a compound of Formula II:

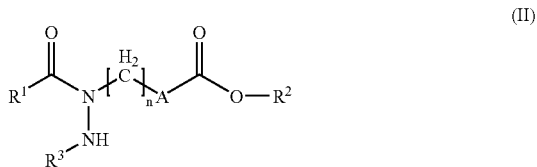

as well as its geometrical isomers, its optically active forms as enantiomers, diastereomers and mixtures of these, as well as salts thereof, wherein A, $R^1$, $R^2$, $R^3$ and n are as defined above.

In a tenth aspect, the invention provides a compound of Formula IV:

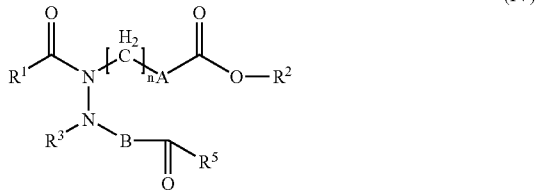

as well as its geometrical isomers, its optically active forms as enantiomers, diastereomers and mixtures of these, as well as salts thereof, wherein A, B, $R^1$, $R^2$, $R^3$, $R^5$ and n are as defined above.

DETAILED DESCRIPTION OF THE INVENTION

The following paragraphs provide definitions of the various chemical moieties that make up the compounds according to the invention and are intended to apply uniformly throughout the specification and claims unless an otherwise expressly set out definition provides a broader definition.

"$C_1$-$C_6$-alkyl" refers to monovalent alkyl groups having 1 to 6 carbon atoms. This term is exemplified by groups such as methyl, ethyl, n-propyl, isopropyl, n-butyl, isobutyl, tert-butyl, pentyl, n-hexyl and the like.

"$C_1$-$C_5$-alkyl" refers to monovalent alkyl groups having 1 to 5 carbon atoms. This term is exemplified by groups such as methyl, ethyl, n-propyl, isopropyl, n-butyl, isobutyl, tert-butyl, pentyl and the like.

"$C_2$-$C_6$-alkenyl" refers to alkenyl groups preferably having from 2 to 6 carbon atoms and having at least 1 or 2 sites of alkenyl unsaturation. Preferable alkenyl groups include ethenyl(—CH=$CH_2$), n-2-propenyl(allyl, —$CH_2$CH=$CH_2$) and the like.

"$C_2$-$C_6$-alkynyl" refers to alkynyl groups preferably having from 2 to 6 carbon atoms and having at least 1-2 sites of alkynyl unsaturation, preferred alkynyl groups include ethynyl(—C≡CH), propargyl(—$CH_2$C≡CH), and the like.

"$C_1$-$C_6$-alkylene" refers to a divalent "$C_1$-$C_6$-alkyl" and by analogy, "$C_2$-$C_6$ alkenylene" refers to a divalent "$C_2$-$C_6$-alkenyl" and "$C_2$-$C_6$ alkynylene"to a divalent "$C_2$-$C_6$-alkynyl".

"$C_1$-$C_6$-heteroalkyl" refers to alkyl groups having 1 to 6 carbon atoms wherein at least 1 carbon atom is replaced by an heteroatom such as O, S or N. This term is exemplified by methoxy, ethoxy, butoxy, aminomethyl, aminoethyl, amino propyl, methyl sulfanyl, ethyl sulfanyl.

"Aryl" refers to an unsaturated aromatic carbocyclic group of from 6 to 14 carbon atoms having a single ring (e.g., phenyl) or multiple condensed rings (e.g., naphthyl). Preferred aryl include phenyl, naphthyl, phenantrenyl and the like.

"Aryl $C_1$-$C_6$-alkyl" refers to $C_1$-$C_6$-alkyl groups having an aryl substituent, including benzyl, phenethyl and the like.

"Heteroaryl" refers to a monocyclic heteroaromatic, or a bicyclic or a tricyclic fused-ring heteroaromatic group. Particular examples of heteroaromatic groups include optionally substituted pyridyl, pyrrolyl, furyl, thienyl, thiophenyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadia-zolyl, 1,2,5-oxadiazolyl, 1,3,4-oxadiazolyl, 1,3,4-triazinyl, 1,2,3-triazinyl, benzofuryl, [2,3-dihydro]benzofuryl, isobenzofuryl, benzothienyl, benzotriazolyl, isobenzothienyl, indolyl, isoindolyl, 3H-indolyl, benzimidazolyl, imidazo[1,2-α]pyridyl, benzothiazolyl, benzoxa-zolyl, quinolizinyl, quinazolinyl, pthalazinyl, quinoxalinyl, cinnolinyl, napthyridinyl, pyrido[3,4-β]pyridyl, pyrido[3,2-β]pyridyl, pyrido[4,3-β]pyridyl, quinolyl, isoquinolyl, tetrazolyl, 5,6,7,8-tetrahydroquinolyl, 5,6,7,8-tetrahydroisoquinolyl, purinyl, pteridinyl, carbazolyl, xanthenyl or benzoquinolyl.

"Heteroaryl $C_1$-$C_6$-alkyl" refers to $C_1$-$C_6$-alkyl groups having a heteroaryl substituent, including 2-firylmethyl, 2-thienylmethyl, 2-(1H-indol-3-yl)ethyl and the like.

"$C_2$-$C_6$-alkenyl" refers to alkenyl groups preferably having from 2 to 6 carbon atoms and having at least 1 or 2 sites of alkenyl unsaturation. Preferable alkenyl groups include ethenyl(—CH=$CH_2$), n-2-propenyl(allyl, —$CH_2$CH=$CH_2$) and the like.

"$C_2$-$C_6$-alkynyl" refers to alkynyl groups preferably having from 2 to 6 carbon atoms and having at least 1-2 sites of alkynyl unsaturation, preferred alkynyl groups include ethynyl (—C≡CH), propargyl(—$CH_2$C≡CH), and the like.

"$C_3$-$C_8$-cycloalkyl" refers to a saturated carbocyclic group of from 3 to 8 carbon atoms having a single ring (e.g., cyclohexyl) or multiple condensed rings (e.g., norbornyl). Preferred cycloalkyl include cyclopentyl, cyclohexyl, norbornyl and the like.

"Heterocycloalkyl" refers to a $C_3$-$C_8$-cycloalkyl group according to the definition above, in which up to 3 carbon atoms are replaced by heteroatoms chosen from the group consisting of O, S, NR, R being defined as hydrogen or methyl. Preferred heterocycloalkyl include pyrrolidine, piperidine, piperazine, 1-methylpiperazine, morpholine, and the like.

"Cycloalkyl $C_1$-$C_6$-alkyl" refers to $C_1$-$C_6$-alkyl groups having a cycloalkyl substituent, including cyclohexylmethyl, cyclopentylpropyl, and the like.

"Heterocycloalkyl $C_1$-$C_6$-alkyl" refers to $C_1$-$C_6$-alkyl groups having a heterocycloalkyl substituent, including 2-(1-pyrrolidinyl)ethyl, 4-morpholinylmethyl, (1-methyl-4-piperidinyl)methyl and the like.

"Alkoxy" refers to the group —O—R where R includes "$C_1$-$C_6$-alkyl" or "aryl" or "heteroaryl" or "$C_1$-$C_6$-alkyl aryl" or "$C_1$-$C_6$-alkyl heteroaryl". Preferred alkoxy groups include by way of example, methoxy, ethoxy, phenoxy and the like.

"Halogen" refers to fluoro, chloro, bromo and iodo atoms.

"Substituted or unsubstituted": Unless otherwise constrained by the definition of the individual substituent, the above set out groups, like "alkyl", "alkenyl", "alkynyl", "aryl", "heteroaryl", "cycloalkyl", "heterocycloalkyl" etc . . . groups can optionally be substituted with from 1 to 5 substituents selected from the group consisting of "$C_1$-$C_6$-alkyl", "$C_2$-$C_6$-alkenyl", "$C_2$-$C_6$-alkynyl", "cycloalkyl", "heterocycloalkyl", "aryl $C_1$-$C_6$-alkyl", "heteroaryl $C_1$-$C_6$-alkyl", "cycloalkyl $C_1$-$C_6$-alkyl", "heterocycloalkyl $C_1$-$C_6$-alkyl", "amino", "ammonium", "acyl", "acyloxy", "acylamnino", "aminocarbonyl", "alkoxycarbonyl", "ureido", "aryl", "carbamate", "heteroaryl", "sulfinyl", "sulfonyl", "alkoxy", "sulfanyl", "halogen", "carboxy", trihalomethyl, cyano, hydroxy, mercapto, nitro, and the like.

"Pharmaceutically acceptable salts or complexes" refers to salts or complexes of the below-specified compounds of Formula (I). Examples of such salts include, but are not restricted, to base addition salts formed by reaction of compounds of Formula (I) with organic or inorganic bases such as hydroxide, carbonate or bicarbonate of a metal cation such as those selected in the group consisting of alkali metals (sodium, potassium or lithium), alkaline earth metals (e.g. calcium or magnesium), or with an organic primary, secondary or tertiary alkyl amine. Amine salts derived from methylamine, dimethylamine, trimethylamine, ethylamine, diethylamine, triethylamine, morpholine, N-Mc-D-glucamine, N,N'-bis(phenylmethyl)-1,2-ethanediamine, tromethamine, ethanolamine, diethanolamine, ethylenediamine, N-methylmorpholine, procaine, piperidine, piperazine and the like are contemplated being within the scope of the instant invention.

Also comprised are salts which are formed from to acid addition salts formed with inorganic acids (e.g. hydrochloric acid, hydrobromic acid, sulfuric acid, phosphoric acid, nitric acid, and the like), as well as salts formed with organic acids such as acetic acid, oxalic acid, tartaric acid, succinic acid, malic acid, fumaric acid, maleic acid, ascorbic acid, benzoic acid, tannic acid, palmoic acid, alginic acid, polyglutamic acid, naphthalene sulfonic acid, naphthalene disulfonic acid, and poly-galacturonic acid.

"Pharmaceutically active derivative" refers to any compound that upon administration to the recipient, is capable of providing directly or indirectly, the activity disclosed herein.

The term "Enantiomeric excess" (ee) refers to the percent excess of the enantiomer over the racemate in a mixture of a pure enantiomer (R or S) and a racemate (RS) as defined below.

$$ee = 100\% \times (|R-S|)/(R+S) = |\%R - \%S|$$

where R represents the number of moles of R enantiomer in the sample and S represents the number of moles of S enantiomer in the sample, and |R−S| represents the Absolute Value of the difference of R and S. Compounds of the invention can be obtained in an "Enantiomeric excess" by a synthesis comprising an enantioselective step or can be isolated by for example, crystallization or chiral HPLC.

A particularly preferred embodiment includes compounds of the invention in an enantiomeric excess of the R enantiomer, of at least at or about 50, 70, 80 or 90%, with degree of preference increasing with the increasing ee of the R enantiomer.

A particularly preferred embodiment includes compounds of the invention in an enantiomeric excess of the S enantiomer, of at least at or about 50, 70, 80 or 90%, with degree of preference increasing with the increasing ee of the S enantiomer.

In the absence of an enantiomeric synthesis, racemic products are usually obtained that do however also have the inventive set out activity as EP2 and/or EP4 agonists.

The term "preterm labor" or the term "premature labor" shall mean expulsion from the uterus of an infant before the normal end of gestation, or more particularly, onset of labor with effacement and dilation of the cervix before the $37^{th}$ week of gestation. It may or may not be associated with vaginal bleeding or rupture of the membranes.

The term "dysmenorrhea" shall mean painful menstruation.

The term "caesarean delivery" shall mean incision through the abdominal and uterine walls for delivery of a foetus.

The term "fertility condition(s)" also refers to a condition, particularly infertility, of a female mammal, especially a female patient. This condition includes conditions where ovulation triggering is needed. Examples of female patients in such a condition are female undergoing a treatment for ovulation induction or an Assisted Technology (ART) therapy. The term "ovulation induction" (OI), refers to the stimulation of release of an oocyte (occasionally two or three oocytes) into the fallopian tubes of a female patient, for in vivo fertilisation. OI is used in anovulatory patients [for example, WHO group I patients (hypogonadotrophic hypogonadism) and WHO group II anovulation (hypothalamic-pituitary dysfunction resulting in arrested or attenuated gonadal function), including patients suffering from polycystic ovarian syndrome (PCOS)]. It is usually desired to stimulate the release of a single oocyte, in order to avoid the risks associated with multiple pregnancies. In a typical ovulation induction regimen, the patient is administered FSH, an analogue of FSH or a molecule stimulating endogenous FSH production to stimulate follicular growth for several days until at least one follicle is observed (by ultrasound) with a mean diameter of approximately 17 mm or greater. At this stage, an ovulation trigger (hCG) is given to stimulate rupture of the follicle and release of an oocyte into the fallopian tube ("ovulation triggering").

The term "Assisted Reproductive Technology" (ART) includes for example, in vitro fertilisation (IVF), and intracytoplasmic sperm injection (ICSI). Oocytes are harvested from mature follicles immediately before rupture, and graded before being fertilized in vitro by combination with sperm.

The resulting embryos are graded for quality, and usually 2 to 3 are selected for placement in the uterus (remaining embryos can be cryo-preserved for future attempts). Because of the many factors involved in establishing an ongoing pregnancy, many patients must have oocytes placed in the uterus multiple times before success is achieved. Because of this, in contrast to OI regimens, for ART it is desired to harvest multiple oocytes, in order to maximise the chances of successful pregnancy. The controlled development of multiple pre-ovulatory follicles by administration of exogenous agents capable of inducing follicular growth (such as FSH) is called controlled ovarian hyperstimulation (COH). When there are at least 3 follicles with a mean diameter greater than 16 mm, ovulation is triggered (hCG bolus). Oocytes are usually recovered from pre-ovulatory follicles, by aspiration.

The present invention also includes the geometrical isomers, the optically active forms, enantiomers, diastereomers of compounds according to Formula I mixtures of these, racemates and also pharmaceutically acceptable salts.

Preferred compounds of the invention are those according to Formula I wherein B, $R^1$, $R^2$, $R^3$, $R^4$, $R^5$ and n are as defined above; A is are selected from the group comprising or consisting of optionally substituted aryl, including phenyl, and optionally substituted heteroaryl.

Further preferred A in compounds according to Formula I is phenyl.

Preferred $R^1$ in compounds according to Formula I is optionally substituted $C_1$-$C_6$ alkyl, including methyl, ethyl and isobutyl.

Preferred $R^2$ in compounds according to Formula I is H.

Preferred $R^3$ in compounds according to Formula I are those selected from the group comprising or consisting of H and methyl.

Further preferred $R^3$ in compounds according to Formula I is H.

Preferred n in compounds according to Formula I is 2.

Preferred B in compounds according to Formula I is optionally substituted $C_1$-$C_6$ alkyl, including ethylene.

Preferred $R^4$ in compounds according to Formula I is H.

Preferred $R^5$ in compounds according to Formula I is selected from the group comprising or consisting of H; optionally substituted $C_1$-$C_6$ alkyl, including methyl and pentyl; optionally substituted aryl $C_1$-$C_6$ alkyl, including optionally substituted phenyl methyl such as phenyl methyl, 3-cyclopropylethynylphenyl methyl, 3-fluorophenyl methyl, 4-fluorophenyl methyl, 4-chlorophenyl methyl, 3-chlorophenyl methyl, 3-iodophenyl methyl, 3-bromophenyl methyl, 4-phenylethynylphenyl methyl, 3-phenylethynylphenyl methyl, 3-ethynylphenyl methyl, biphenyl-3-yl methyl, 3-trifluoromethylphenyl methyl; optionally substituted heteroaryl $C_1$-$C_6$ alkyl, including optionally thienyl-2-yl and optionally substituted $C_3$-$C_8$ cycloalkyl, including cyclohexyl.

A particularly preferred embodiment of the present invention is a hydrazide derivative according to Formula I wherein A is phenyl; B is ethylene; $R^1$ is optionally substituted $C_1$-$C_6$ alkyl, including methyl, ethyl and isobutyl; $R^2$ and $R^4$ are H; $R^5$ is selected from the group comprising or consisting of H and optionally substituted $C_1$-$C_6$ alkyl, including methyl and pentyl and n is 2.

Another preferred embodiment of the present invention is hydrazide derivative according to Formula I wherein A is phenyl; B is ethylene; $R^1$ is optionally substituted $C_1$-$C_6$ alkyl, including methyl, ethyl and isobutyl; $R^2$ and $R^4$ are H; $R^5$ is optionally substituted aryl $C_1$-$C_6$ alkyl, including optionally substituted phenyl methyl such as phenyl methyl, 3-cyclopropylethynylphenyl methyl, 3-fluorophenyl methyl, 4-fluorophenyl methyl, 4-chlorophenyl methyl, 3-chlorophenyl methyl, 3-iodophenyl methyl, 3-bromophenyl methyl, 4-phenylethynylphenyl methyl, 3-phenylethynylphenyl methyl, 3-ethynylphenyl methyl, biphenyl-3-yl methyl, 3-trifluoromethylphenyl methyl.

Another preferred embodiment of the present invention is hydrazide derivative according to Formula I wherein A is phenyl; B is ethylene; $R^1$ is optionally substituted $C_1$-$C_6$ alkyl, including methyl, ethyl and isobutyl; $R^2$ and $R^4$ are H; $R^5$ is optionally substituted heteroaryl $C_1$-$C_6$ alkyl, including optionally thienyl-2-yl.

Another preferred embodiment of the present invention is hydrazide derivative according to Formula I wherein A is phenyl; B is ethylene; $R^1$ is optionally substituted $C_1$-$C_6$ alkyl, including methyl, ethyl and isobutyl; $R^2$ and $R^4$ are H; $R^5$ is optionally substituted $C_3$-$C_8$ cycloalkyl, including cyclohexyl.

According to a preferred embodiment of the invention, a hydrazide derivative of the invention is selected from the group consisting of:
4-(2-{1-acetyl-2-[4-(3-chlorophenyl)-3-hydroxybutyl] hydrazino}ethyl)benzoic acid;
4-(2-{1-acetyl-2-[3-hydroxy-4-(3-iodophenyl)butyl] hydrazino}ethyl)benzoic acid;
4-(2-{1-acetyl-2-[4-(3-bromophenyl)-3-hydroxybutyl] hydrazino}ethyl)benzoic acid;
4-(2-{1-acetyl-2-[4-(1,1'-biphenyl-3-yl)-3-hydroxybutyl] hydrazino}ethyl)benzoic acid;
4-[2-(1-acetyl-2-{3-hydroxy-4-[3-(phenylethynyl)phenyl] butyl}hydrazino)ethyl]benzoic acid;
4-{2-[1-acetyl-2-(3-hydroxy-4-phenylbutyl)hydrazino] ethyl}benzoic acid;
4-(2-{1-acetyl-2-[4-(4-chlorophenyl)-3-hydroxybutyl] hydrazino}ethyl)benzoic acid;
4-(2-{1-acetyl-2-[4-(4-fluorophenyl)-3-hydroxybutyl] hydrazino}ethyl)benzoic acid;
4-(2-{1-acetyl-2-[4-(3-ethynylphenyl)-3-hydroxybutyl] hydrazino}ethyl)benzoic acid;
4-(2-{1-acetyl-2-[4-(3-fluorophenyl)-3-hydroxybutyl] hydrazino}ethyl)benzoic acid;
4-[2-(1-acetyl-2-{3-hydroxy-4-[4-(phenylethynyl)phenyl] butyl}hydrazino)ethyl]benzoic acid;
4-{2-[1-acetyl-2-(3-hydroxy-4thien-2-ylbutyl)hydrazino] ethyl}benzoic acid;
4-[2-(1-acetyl-2-{4-[3-cyclopropylethynyl)phenyl]-3-hydroxybutylhydrazino)ethyl]benzoic acid;
4-[2-(2-{3-hydroxy-4-[3-(trifluoromethyl)phenyl]butyl}-1-isobutyrylhydrazino)ethyl]benzoic acid;
4-[2-(2-{3-hydroxy-4-[3-(trifluoromethyl)phenyl]butyl}-1-propionylhydrazino)ethyl]benzoic acid;
4-[2-(1-acetyl-2-{3-hydroxy-4-[3-(trifluoromethyl)phenyl] butyl}hydrazino)ethyl]benzoic acid;
4-{2-[1-acetyl-2-(3-cyclohexyl-3-hydroxypropyl)hydrazino]ethyl}benzoic acid; or a pharmaceutically acceptable salt of any of said compounds.

According to another preferred embodiment of the invention, a hydrazide derivative of the invention is selected from the group consisting of:
4-{2-[1-acetyl-2-(3-hydroxyoctyl)hydrazino]ethyl}benzoic acid;
4-{2-[1-acetyl-2-(3-hydroxyoctyl)-2-methylhydrazino] ethyl}benzoic acid;
4-{2-[1-acetyl-2-(3-hydroxybutyl)hydrazino]ethyl}benzoic acid; or a pharmaceutically acceptable salt of any of said compounds.

Compounds of Formula I may be used as a medicament.

Specifically, the compounds of Formula I are suitable for use in treating disorders such as premature birth; dysmenorrhea; and for stopping labor prior to cesarean delivery; respiratory disorders including asthma, emphysema and chronic obstructive pulmonary disorder (COPD); glaucoma; hypertension; gastric ulcers; renal dysfunction; osteoporosis and other destructive bone disease or disorder; immune deficiency disorders; sexual dysfunction; including erectile dysfunction; fertility disorders, including ovulatory disorders and inflammatory disorders including Inflammatory Bowel Disease (TBD), Crohn's disease, joint inflammation and pulmonary inflammation.

In a further aspect, the invention provides a use of a hydrazide derivatives compound of Formula I for the treatment or prevention (including prophylactic treatment) of a disease or condition as disclosed herein, including premature birth; dysmenorrhea; and for stopping labor prior to cesarean delivery; respiratory disorders including asthma, emphysema and chronic obstructive pulmonary disorder (COPD); glaucoma; hypertension; gastric ulcers; renal dysfunction; osteoporosis and other destructive bone disease or disorder; immune deficiency disorders; sexual dysfunction; including erectile dysfunction; fertility disorders; including ovulatory disorders and inflammatory disorders including Inflammatory Bowel Disease (IBD), Crohn's disease, joint inflammation and pulmonary inflammation.

In a yet further aspect, the invention provides a use of a hydrazide derivative compound of Formula I for the preparation of a medicament for the treatment or prevention (including prophylactic treatment) of a disease or condition as disclosed herein, including premature birth, dysmenorrhea, and for stopping labor prior to cesarean delivery, asthma, glaucoma, hypertension, gastric ulcers, renal dysfunction, osteoporosis and other destructive bone disease or disorder, immune deficiency disorders and sexual dysfunction, including erectile dysfunction, fertility disorders, including ovulatory disorders and inflammatory disorders including Inflammatory Bowel Disease (IBD), Crohn's disease, joint inflammation and pulmonary inflammation.

In a yet further aspect, the invention provides a method for the treatment and/or prevention of disorders selected from premature birth, dysmenorrhea, and for stopping labor prior to cesarean delivery; respiratory disorders including asthma, emphysema and chronic obstructive pulmonary disorder (COPD); glaucoma; hypertension; gastric ulcers; renal dysfunction; osteoporosis and other destructive bone disease or disorder; immune deficiency disorders sexual dysfunction; including erectile dysfunction; fertility disorders; including ovulatory disorders and inflammatory disorders including Inflammatory Bowel Disease (IBD), Crohn's disease, joint inflammation and pulmonary inflammation. The method for treatment according to the invention, comprises the administration of a hydrazide compound according to Formula (I), in a patient in need thereof.

Preferred methods of the invention including identifying and/or selecting a subject (e.g. mammal, particularly human) that is susceptible to or suffering from a condition disclosed herein, and thereafter administering to the identified and selected subject one or more compounds of the invention, particularly a subject that is identified and selected as being susceptible to or suffering from premature birth, dysmenorrhea, and for stopping labor prior to cesarean delivery; respiratory disorders including asthma, emphysema and chronic obstructive pulmonary disorder (COPD); glaucoma; hypertension; gastric ulcers; renal dysfunction; osteoporosis and other destructive bone disease or disorder; immune deficiency disorders sexual dysfunction; including erectile dysfunction; fertility disorders; including ovulatory disorders and inflammatory disorders including Inflammatory Bowel Disease (IBD), Crohn's disease, joint inflammation and pulmonary inflammation.

The invention also provides pharmaceutical compositions that comprise one or more hydrazide derivatives compounds of Formula I together with a suitable carrier for the compound(s).

Preferably, the compounds according to Formula I alone or in a form of a pharmaceutical composition are suitable for the modulation of EP function(s), thus specifically allowing the treatment and/or prevention of disorders which are mediated by the EP receptors. Such modulation preferably involves the agonisation of EP function(s), notably by the agonisation of the EP2 and/or EP4 receptors in mammals, and in particular in humans.

Preferred prostaglandin EP2 and or EP4 receptor agonists exhibit activity in a prostaglandin EP2 and/or EP4 receptor binding assay, an example thereof is defined in the protocol as defined in Examples 22 and 24, which follow.

Other preferred prostaglandin EP2 and or EP4 receptor agonists exhibit activity in a cAMP assay on cell lines over-expressing EP4 receptor, an example thereof is defined in the protocol as defined in Examples 23 and 25, which follow.

Other preferred methods of the invention are methods including administering compounds of Formula I to a subject susceptible to or suffering from a disorder selected from infertility, fertility disorder, including female infertility and ovulatory disorders, asthma, bone diseases, inflammnatory disorders and sexual dysfunction, including erectile dysfunction.

The compounds of the invention may be employed alone or in combination with further pharmaceutical agents, e.g. with a further EP modulator or any other substance used such as FSH, LH, mixtures of these and hCG, during the ovulation induction or ART therapies.

When employed as pharmaceuticals, the hydrazide derivatives of the present invention are typically administered in the form of a pharmaceutical composition. Hence, pharmaceutical compositions comprising a compound of Formula I and a pharmaceutically acceptable carrier, diluent or excipient are also within the scope of the present invention. A person skilled in the art is aware of a whole variety of such carriers, diluents or excipients suitable to formulate a pharmaceutical composition.

The compounds of the invention, together with a conventionally employed adjuvant, carrier, diluent or excipient may be formulated as pharmaceutical compositions and unit dosages thereof, and in such form may be employed as solids, such as tablets or filled capsules, or liquids such as solutions, suspensions, emulsions, elixirs, or capsules filled with the same, all for oral use, or in the form of sterile injectable solutions for parenteral (including subcutaneous) use. Such pharmaceutical compositions and unit dosage forms thereof may comprise ingredients in conventional proportions, with or without additional active compounds or principles, and such unit dosage forms may contain any suitable effective amount of the active ingredient commensurate with the intended daily dosage range to be employed.

When employed as pharmaceuticals, the amino derivatives of this invention are typically administered in the form of a pharmaceutical composition. Such compositions can be prepared in a manner well known in the pharmaceutical art and comprise at least one active compound. Generally, the compounds of this invention are administered in a pharmaceutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The pharmaceutical compositions of the invention can be administered by a variety of routes including oral, rectal, transdermal, subcutaneous, intravenous, intramuscular, and intranasal. Depending on the intended route of delivery, the compounds are preferably formulated as either injectable or oral compositions. The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampoules or syringes of the liquid compositions or pills, tablets, capsules or the like in the case of solid compositions. In such compositions, the amino compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or non-aqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatine; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as pepper-mint, methyl salicylate, or orange flavoring.

Injectable compositions are typically based upon injectable sterile saline or phosphate-buffered saline or other injectable carriers known in the art. As above mentioned, the hydrazide derivatives of Formula I in such compositions is typically a minor component, frequently ranging between 0.05 to 10% by weight with the remainder being the injectable carrier and the like.

The components described above for orally administered or injectable compositions are merely representative. Further materials as well as processing techniques and the like are set out in Part 8 of *Remington's Pharmaceutical Sciences*, 20$^{th}$ Edition, 2000, Merck Publishing Company, Easton, Pa.

The compounds of this invention can also be administered in sustained release forms or from sustained release drug delivery systems. A description of representative sustained release materials can also be found in *Remington's Pharmaceutical Sciences*, 20$^{th}$ Edition, 2000, Marck Publishing Company, Easton, Pa.

Still a further embodiment is a process for preparing a hydrazide of Formula I, comprising the step of a reductive amination of a hydrazide of Formula II with a compound of Formula III in presence of a reducing agent, preferably NaCNBH$_3$ in MeOH.

Still a further embodiment of the invention is a process for preparing a hydrazide of Formula I, comprising the step of a reductive amination of a hydrazide of Formula II with a compound of Formula III in presence of a reducing agent, preferably NaCNBH$_3$ in MeOH.

Another embodiment of the invention is a process for preparing a hydrazide of Formula I, comprising the step of a reduction of a compound of Formula IV in presence of a hydride, preferably with the combination of sodium borohydride and CeCl$_3$.

Another embodiment of the invention is a process for preparing a hydrazide of Formula I, comprising the step of a reduction of a compound of Formula IV in presence of a hydride, preferably with the combination of sodium borohydride and CeCl$_3$ and further comprising the step an addition of compound of Formula V to a compound o formula II through a Michael addition, for example in presence of NEt$_3$ in MeOH.

Another preferred embodiment of the invention is a process for preparing a hydrazide of Formula I, further comprising the step of saponification of the resulting compound of Formula I wherein R$^1$ is not H, for example in presence of NaOH in MeOH/THF/water into a compound of Formula I wherein R$^2$ is H.

Another further preferred embodiment of the invention is a process for preparing a hydrazide of Formula I wherein A is phenyl.

Another preferred embodiment of the invention provides a compound of Formula II wherein A is optionally substituted aryl such as phenyl; R$^1$, R$^2$ and R$^3$ are as defined above.

Another preferred embodiment of the invention provides a compound of Formula IV, wherein A is optionally substituted aryl such as phenyl; B, R$^1$, R$^2$, R$^3$ and R$^5$ are as defined above.

Another further preferred embodiment of the invention provides a compound of Formula IV, wherein A is optionally substituted aryl such as phenyl; B is ethyl; R$^1$, R$^2$, R$^3$ and R$^5$ are as defined above.

The hydrazide derivatives exemplified in this invention may be prepared from readily available or previously described starting materials using the following general methods and procedures. It will be appreciated that where typical or preferred experimental conditions (i.e. reaction temperatures, time, moles of reagents, solvents, etc.) are given, other experimental conditions can also be used unless otherwise stated. Optimum reaction conditions may vary with the particular reactants or solvents used, but such conditions can be determined by one skilled in the art by routine optimisation procedures.

Synthesis of Compounds of the Invention:

The novel hydrazide derivatives can be prepared from readily available starting materials Examples of synthetic pathways for compounds of Formula I will be described below.

Abbreviations:

The following abbreviations refer respectively to the definitions below: g (gram), hr (hour), i.p. (interperitoneal), i.v. (intravenous), mg (milligram), µg (microgram), min (minute), mm (millimeter), mmol (millimole), mM (millimolar), p.o. (per os), mL (milliliter), µL (microliter), MHz (Megahertz.), ACN (Acetonitrile), BAIB [Bis(acetoxy)iodo] benzene, BSA (Bovine Serum Albumin), cAmP (Cyclic Adenosine Monophosphate), CMC (Carboxymethyl Cellulose), COPD (Chronic Obstructive Pulmonary Disease), DIEA (diisopropyl ethylamine), DCM (Dichloromethane), DMAP (4-dimethylamino-pyridine), DMF (dimethylformamide), DMSO (Dimethylsulfoxide), DSS (Dextran Sodium Sulfate), DXA (Dual-energy X-ray absorptiometry), EDTA (ethylenediaminetetraacetic acid), EP2 (Prostaglandin E2), EP4 (Prostaglandin E4), EtOAc (Ethyl acetate), FBS (Foetal Bovine Serum), hCG (human Chorionic Gonadotrophin), IT (Intratracheal), MEM (Dulbecco's Modified Eagle Media), N.A. (not available), NMR (Nuclear Magnetic Resonance), PBS (Phosphate Buffer Saline), NP3S (5% N-methyl-pyrrolidinone/30% PEG400/25% PFG200/20% Propylene glycol in saline), PGE1 (Prostaglandin E1), PGE2 (Prostaglandin E2), PEG (Polyethylene glycol), PMSG (Pregnant mare's serum gonadotropin), PSS (Physiologic salt solution), PVT (polyvinyl toluene), RP-HPLC (Reverse Phase High Performance Liquid Chromatography), RT (Room temperature), SC (subcutaneous); SPA (Scintillation Proximity Assay), TBAF (tetrabutylammonium fluoride), TBDMS (t-Butyldimethylsiloxy), TBTU (O-benzotriazolyl-N,N,N',N'-tetramethyl-uronium-tetrafluoro-borate), TEMPO (2,2,6,6-Tetramethyl-1-piperidinyloxyl), TFA (Trifluoro-acetic acid), THF (Tetrahydrofuran), RT (room temperature).

General Protocol:

Synthesis of the hydrazide derivatives of general Formula (xii), i.e. of Formula I wherein $R^2$ is H, were obtained as outlined in Scheme 1 below.

by acidic treatment and the resulting hydrazide intermediate (vi) underwent a Michael addition with the appropriate vinyl ketone (vii) to afford the ketone (viii). Reduction of the ketone group was carried out with a hydride, such as the combination of sodium borohydride and cerium (III) chloride, to afford the alcohol (xi) in almost quantitative yield.

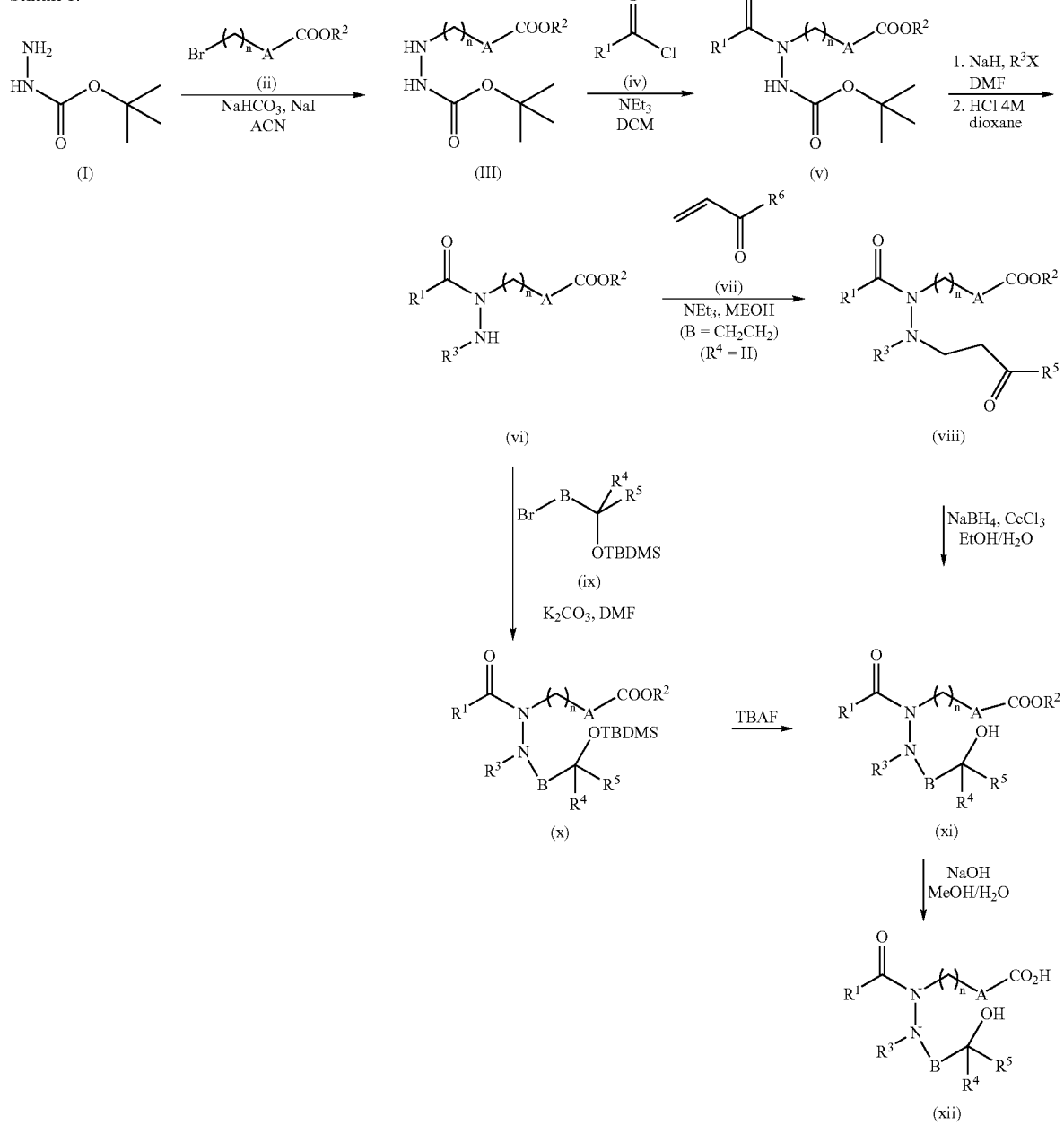

Tert-Butyl carbazates (i) was alkylated with the appropriated alkyl halide (ii) in presence of a suitable base, such as sodium bicarbonate, and treated with the appropriate acyl chloride (iv) to afford the intermediate (v). The carbazate intermediate could then be alkylated/acylated with the appropriate halide derivative in the presence of a suitable base like NaH. Removal of the tert-butylcarbamate group was obtained by acidic treatment and the resulting hydrazide intermediate Alkylation of the hydrazide intermediate (vi) could also be obtained using the general alkyl bromide (ix) to afford the intermediate (x). The free alcohol could then be obtained by treatment with TBAF or other suitable agents to afford the desired intermediate (xi). Saponification of the ester group using NaOH in methanol/THF/water gave the final product (xii) in good yield.

17

The enantio-selective synthesis of these derivatives is described in Scheme 2 below:

Scheme 2:

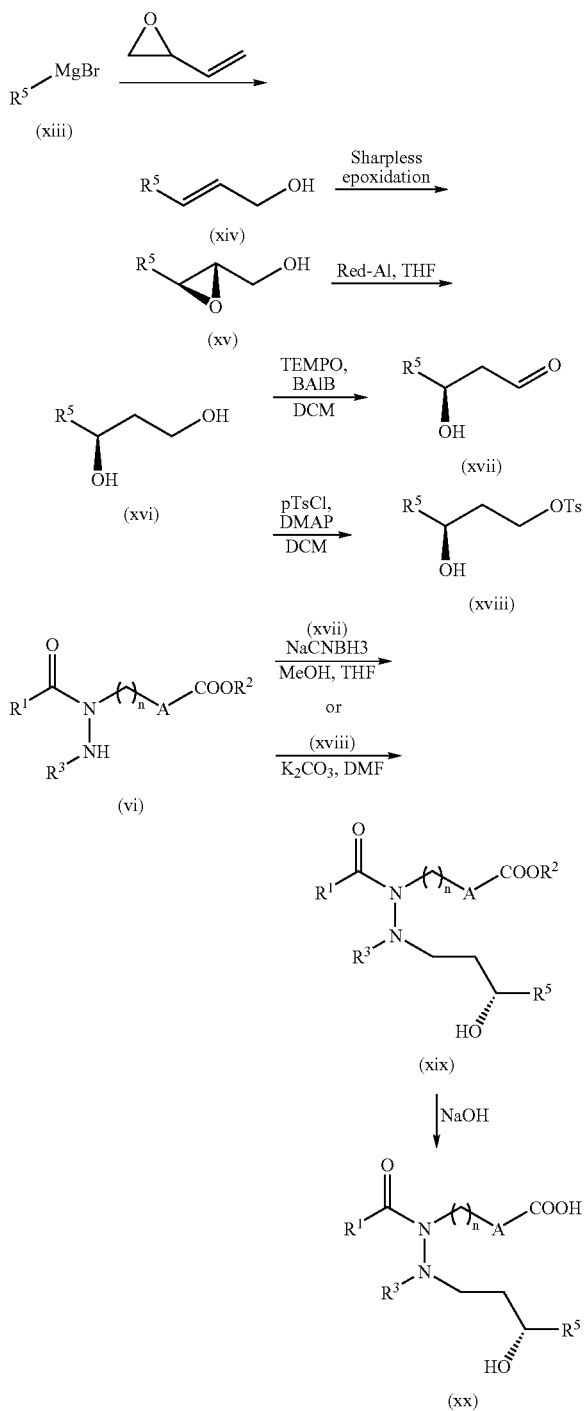

The enantioselective synthesis of derivatives of Formula (I) wherein $R^2$ and $R^4$ are H and B is $CH_2CH_2$, i.e. of formula (xx) is described in Scheme 2 above. The commercially available butadiene monoxide was converted to allylic alcohol (xiv) by reaction with Grignard reagent (xiii) (commercially available or obtained from bromide and Mg in ether as described in Meltzer et al., 1993). The allylic alcohol intermediate was then subjected to the Sharpless epoxidation condition (Sharpless et al., 1987) with (−)-diethyl D-tartrate to furnish the epoxide (xv). Regio-selective ring opening of the epoxide with Red-Al (Sharpless et al., 1982) afforded the diol derivative (xvi) in good yield. Selective oxidation of the primary alcohol using TEMPO and BAID (Piancatelli et al., 1997) afforded the aldehyde intermediate (xvii). Reductive amination reaction between this aldehyde and the hydrazide intermediate (vi) using NaCNBH$_3$ in MeOH afforded the alcohol intermediate (xix). Alkylation of the hydrazide intermediate (vi) could also be obtained using the tosylate intermediate (xviii) obtained from the 1,3-diol derivative (xvi) and paratoluensulfonyl chloride. Finally, deprotection of the ester intermediate (xix) afforded the desired compound (xx), i.e. of Formula (I) wherein $R^2$ and $R^4$ are H and B is $CH_2CH_2$ in good yield and excellent optical purity.

EXAMPLES

The invention will be illustrated by means of the following examples which are not to be construed as limiting the scope of the invention.

The compounds of the present invention may be synthesized according to the different synthesis pathways provided above. The following examples illustrate preferred methods for synthesizing the compounds according to Formula I, and for determining their biological activities.

Example 1

4-{2-[1-acetyl-2-(3-hydroxybutyl)hydrazino]ethyl}benzoic acid

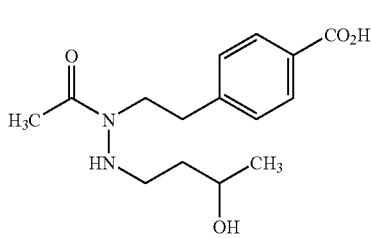

Intermediate 1.1: methyl 4-(2-bromoethyl)benzoate

To a solution of p-bromoethyl benzoic acid (4.58 g, 0.02 mol), commercially available from Pfaltz-Bauer, in DCM (40 mL) and MeOH (20 mL) was added trimethylsilyldiazomethane (11 mL, 2.0 M in hexanes) at room temperature dropwise. The mixture was stirred for 2 hours and the solvent was removed to afford intermediate 1.1 (5.0 g, 100% yield) as colorless oil used in the next step without further purification.

Intermediate 1.2: tert-butyl2-{2-[4-(methoxycarbonyl)phenyl]ethyl}hydrazine carboxylate To a solution of intermediate 1.1 (3.5 g, 14.4 mmol) and t-butyl carbazate (2.09 g, 17.3 mmol), commercially available from Acros, in acetonitrile (75 mL) was added sodium bicarbonate (1.45 g, 17.3 mmol) and catalytic amount of sodium iodide and the reaction mixture was refluxed for 18 h. The salt was then filtered and the solvent was removed. The resulting solution was diluted with FtOAc and washed with brine. The organic solution was dried over sodium sulfate, concentrated in vacuo and purified by flash chromatography using EtOAc/DCM as eluent to afford intermediate 1.2 (2.34 g, 56% yield) as white solid. R$_f$ 0.5 (FtOAc/DCM 1:2); $^1$H NMR (CDCl$_3$) δ 1.45 (s, 9H), 2.82 (t, J=7.32 Hz, 2H), 3.13 (t, J=7.32 Hz, 2H), 3.90 (s, 3H), 7.27 (d, J=8.04 Hz, 2H), 7.95 (d, J=8.04 Hz, 2H).

Intermediate 1.3: tert-butyl 2-acetyl-2-{2-[4-(methoxycarbonyl)phenyl]ethyl}hydrazine carboxylate To a solution of intermediate 1.2 (200 mg, 0.68 mmol) in pyridine (10 mL) was added acetic anhydride (2.0 mL) and the mixture was stirred at room temperature for 18 hours. The pyridine was removed in vacuum and the crude was diluted with ETOAc (50 mL) and was washed with 2% HCl solution (25 mL), brine and dried over sodium sulfate. The organic solution was then concentrated in vacuo to afford intermediate 1.3 (273 mg, 100%) as pale yellow oil used in the next step without further purification. $^1$H NMR (CDCl$_3$) δ 1.45 (s, 9H), 2.05 (s, 3H), 2.82 (m, 2H), 3.13 (m, 2H), 3.90 (s, 3H), 7.27 (d, J=8.04 Hz, 2H), 7.95 (d, J=8.04 Hz, 2H).

Intermediate 1.4: methyl 4-[2-(1-acetylhydrazino)ethyl]benzoate

To a solution of crude intermediate 1.3 (273 mg, 0.81 mmol) in MeOH (2.0) was added HCl (6.0 mL, 4M HCl in dioxane) and the mixture was stirred at room temperature for 1 hour. The solvent was then removed in vacuo to afford the title compound (248 mg) as colorless oil used in the next step without further purification. M/S (m/z): 237 (M+1).

Intermediate 1.5: methyl 4-{2-[1-acetyl-2-(3-oxobutyl)hydrazino]ethyl}benzoate

To a solution of intermediate 1.4 (248 mg, 1.06 mmol) in MeOH (10 mL) was added triethyl amine (557 μL, 4.2 mmol) and methyl vinyl ketone (332 μL, 4.2 mmol) and the reaction mixture was refluxed for 3 hours. The solvent was then removed in vacuo and the crude was diluted with EtOAc. The organic solution was washed with brine, dried over sodium sulfate and concentrated to afford intermediate 1.4 (300 mg) as colorless oil used in the next step without further purification. M/S (m/z): 307 (M+1).

Intermediate 1.6: methyl 4-{2-[1-acetyl-2-(3-hydroxybutyl)hydrazino]ethyl}benzoate To a solution of crude intermediate 1.5 (300 mg, 1.06 minol) in MeOH (6 mL) and water (10 mL) was added CeCl$_3$·7H$_2$O (394 mg, 1.06 mmol) followed by NaBH$_4$ (57 mg, 1.59 mmol) at −15° C. After 15 minutes the solvent was removed and the crude was diluted with EtOAc. The organic solution was washed with brine, dried over sodium sulfate, concentrated to afford intermediate 1.6 used in the next step without further purification. M/S (m/z): 309 (M+1).

Example 1

4-{2-[1-acetyl-2-(3-hydroxybutyl)hydrazino]ethyl}benzoic acid

To a solution of intermediate 1.6 (300 mg) in THF (3 mL), McOH (3 mL) and water (1 mL) was added NaOH (200 mg, 5 mmol) and the resulting solution was stirred at RT for 5 hours. The solvent was removed in vacuo and the crude mixture was purified by RP-HPLC using ACN/H$_2$O (0.1% TFA) to afford compound (1): $^1$H NMR (CD$_3$OD) δ 1.16 (d, J=6.24 Hz, 3H), 1.53 (m, 1H), 2.12 (s, 3H), 2.82 (m, 2H), 2.95 (m, 2H), 3.13 (m, 2H), 3.78 (m, 2H), 3.82 (m, 1H), 7.35 (d, J=8.04 Hz, 2H), 7.95 (d, J=8.04 Hz, 2H); M/S (m/z): 395.2 (M+1).

Example 2

4-{2-[1-acetyl-2-(3-hydroxyoctyl)hydrazino]ethyl}benzoic acid

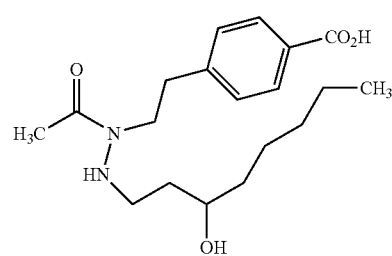

(2)

Intermediate 2.1: methyl 4-{2-[1-acetyl-2-(3-oxooctyl)hydrazino]ethyl}benzoate

To a solution of intermediate 1.4 (208 mg, 0.88 mmol) in MeOH (10 mL) was added triethylamine (488 μL, 3.52 mmol) and 1-octen-3-one (111 mg, 0.88 mmol) and the resulting solution was refluxed for 4 hours. The solvent was then removed in vacuo and the crude was diluted with EtOAc. The organic solution was washed with brine, dried over sodium sulfate and concentrated to afford intermediate 2.1 (200 mg) as colorless oil used in the next step without further purification. M/S (m/z): 363 (M+1).

Intermediate 2.2: methyl 4-{2-[1-acetyl-2-(3-hydroxyoctyl)hydrazino]ethyl}benzoate To a solution of crude intermediate 2.1 (200 mg, 0.88 mmol) in MeOH (6 mL) and water (10 mL) was added CeCl$_3$·7H$_2$O (328 mg, 1.06 mmol) followed by NaBH$_4$ (50 mg, 1.32 mmol) at −15° C. After 15 minutes the solvent was removed and the crude was diluted with EtOAc. The organic solution was washed with brine, dried over sodium sulfate, concentrated to afford intermediate 2.2 used in the next step without further purification. M/S (m/z): 364 (M+1).

Example 2

4-{2-[1-acetyl-2-(3-hydroxyoctyl)hydrazino]ethyl}benzoic acid

To a solution of intermediate 2.2 (200 mg) in THF (3 mL), MeoH (3 mL) and water (1 mL) was added NaOH (200 mg, 5 mmol) and the resulting solution was stirred at RT for 5 hours. The solvent was removed in vacuo and the crude mixture was purified by RP-HPLC using ACN/H$_2$O (0.1% TFA) to afford compound (2): $^1$H NMR (CD3OD) δ 0.90 (m, 3H), 1.32-1.45 (m, 10H), 1.53 (m, 1H), 2.12 (s, 3H), 2.82 (m, 2H), 2.95 (m, 2H), 3.13 (m, 2H), 3.60 (m 1H), 3.78 (m, 2H), 7.35 (d, J=8.04 Hz, 2H), 7.95 (d, J=8.04 Hz, 2H); M/S (m/z): 351.3 (M+1).

Example 3

4-{2-[1-acetyl-2-(3-hydroxyoctyl)-2-methylhydrazino]ethyl}benzoic acid

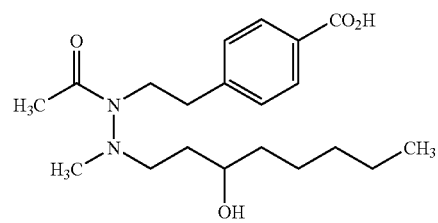

(3)

Intermediate 3.1: tert-butyl 2-acetyl-2-{2-[4-(methoxycarbonyl)phenyl]ethyl}-1-methylhydrazinecarboxylate To a solution of intermediate 1.3 (800 mg, 2.38 mmol) in DMF (10 mL) was added sodium hydride (66 mg, 2.85 mmol) and methyl iodide (177 µL, 2.85 mmol) and the resulting solution was stirred at room temperature for 2 hours. Then the DMF was removed in vacuo and the crude was diluted with EtOAc, washed with brine, dried over sodium sulfate, concentrated to afford to afford the title compound (3.1) as oil used in the next step without further purification. $^1$H NMR (CDCl$_3$) δ 1.45 (s, 9H), 2.05 (s, 3H), 2.82 (m, 2H), 2.90 (s, 3H), 3.80 (m, 2H), 3.90 (s, 3H), 7.27 (d, J=8.04 Hz, 2H), 7.95 (d, J=8.04 Hz, 2H). M/S (m/z): 372 (M+Na).

Intermediate 3.2: methyl 4-[2-(1-acetyl-2-methylhydrazino)ethyl]benzoate

To a solution of intermediate 3.1 (560 mg, 1.6 mmol) in MeOH (2.0) was added HCl (6.0 mL, 4M HCl in dioxane) and the mixture was stirred at room temperature for 1 hour. The solvent was removed in vacuo to afford intermediate 3.2 (400 mg) as colorless oil used in the next step without further purification. M/S (m/z): 251 (M+1).

Intermediate 3.3: methyl 4-{2-[1-acetyl-2-methyl-2-(3-oxooctyl)hydrazino]ethyl}benzoate To a solution of intermediate 3.2 (400 mg, 1.6 mmol) in isopropyl alcohol (10 mL) was added triethylamine (2.2 mL, 16 mmol) and 1-octen-3-one (1.0 g, 8 mmol) and the resulting solution was refluxed for 1 hour. The solvent was then removed in vacuo and the crude diluted with EtOAc. The organic solution was washed with brine, dried over sodium sulfate and concentrated to afford intermediate 3.3 as colorless oil used in the next step without further purification. M/S (m/z): 377.1 (M+1).

Intermediate 3.4: methyl 4-{2-[1-acetyl-2-(3-hydroxyoctyl)-2-methylhydrazino]ethyl}benzoate To a solution of intermediate 3.3 in MeOH (5 mL) and water (5 mL) was added CeCl$_3$.7H$_2$O (596 mg, 1.6 mmol) followed by NaBH$_4$ (93 mg, 1.32 mmol) at −15° C. After 15 minutes the solvent was removed and the crude was diluted with EtOAc. The organic solution was washed with brine, dried over sodium sulfate, concentrated to afford the title compound (3.4) used in the next step without further purification. M/S (m/z): 379 (M+1).

Example 3

4-{2-[1-acetyl-2-(3-hydroxyoctyl)-2-methylhydrazino]ethyl}benzoic acid

To a solution of intermediate 3.4 (200 mg) in THF (3 mL), MeOH (3 mL) and water (1 mL) was added NaOH (200 mg, 5 mmol) and the resulting solution was stirred at RT for 5 hours. The solvent was removed in vacuo and the crude mixture was purified by RP-HPLC using ACN/H$_2$O (0.1% TFA) to afford compound (3): $^1$H NMR (CD$_3$OD) δ 0.90 (m, 3H), 1.32-1.45 (m, 10H), 2.15 (s, 3H), 2.48 (d, 3H), 2.82 (m, 2H), 2.95 (m, 2H), 3.13 (m, 2H), 3.64 (m 1H), 7.35 (d, J=8.04 Hz, 2H), 7.95 (d, J=8.04 Hz, 2H); M/S (m/z): 365.3 (M+1).

Example 4

4-[2-(1-acetyl-2-{3hydroxy-4-[3-(trifluoromethyl)phenyl]butyl}hydrazino)ethyl]benzoic acid

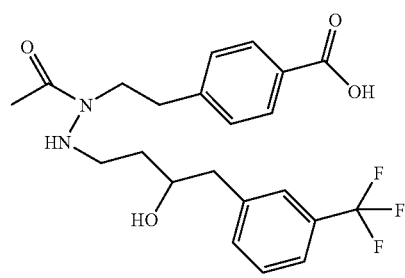

(4)

Intermediate 4.1: N-methoxy-N-methyl-2-[3-(trifluoromethyl)phenyl]acetamide

To a solution of 3-(trifluoromethyl)phenylacetic acid (2.04 g, 10 mmol) and N,O-dimethylhydroxylamine hydrochloride (1.07 g, 11 mmol) in DMF was added HATU (3.8 g, 10 mmol) and DIEA (6.99 ml, 40 mmol) and the resulting yellow solution was stirred at RT for overnight. The crude solution was then extracted with EtOAc and wash with NaHCO$_3$ solution (5%), HCl solution (1:9 v/v) and brine, dried with sodium sulfate and concentrate to afford 2.66 gram of colorless oil as desired compound (4.1) used in the next step without further purification. R$_f$ 0.5 (EtOAc/Hexane 1:1) MS (m/z): 248.1 (M+H), $^1$H NMR (CDCl$_3$) δ 3.2 (s, 3H), 3.65 (s, 3H), 3.80 (s, 2H), 7.40-7.55 (m, 4H).

Intermediate 4.2: 1-[3-(trifluoromethyl)phenyl]but-3-en-2-one

To a solution of intermediate 4.1 (1.0 g, 4 mmol) in THF at 0° C. was added vinyl magnesium bromide (1.0 M in THF, 8 mL, 8.0 mmol) dropwise and the resulting yellow solution was stirred at 0° C. for 20 minutes. Then the reaction was quenched with 2 mL of saturated NH$_4$Cl solution. The crude mixture was then extracted with EtOAc and washed with brine, dried with Na$_2$SO$_4$, concentrated to afford 2.0 gram yellow oil as desired product (4.2) used in the next step without further purification. R$_f$ 0.7 (FtOAc/Hexane 1:3).

Compound of Example 4: 1-[3-(trifluoromethyl)phenyl]but-3-en-2-one

The title compound of Example 4 (4) was prepared from intermediate 1.4 and intermediate 4.2, using the procedure described for Example 1. MS (m/z): 439.4 (M+H), $^1$H NMR (MeOD) δ 1.45-1.60 (m, 2H), 2.20 (s, 3H), 2.80-3.13 (m, 6H), 3.75 (m, 2H), 3.9-4.0 (m, 1H), 7.30 (d, J=8.04 Hz, 2H), 7.45-7.55 (m, 4H), 7.95 (d, J=8.04 Hz, 2H).

Example 5

4-[2-(2-{3-hydroxy-4-[3-(trifluoromethyl)phenyl]butyl}-1-propionyl hydrazino)ethyl]benzoic acid

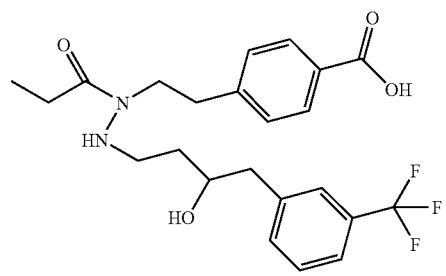

(5)

Intermediate 5.1: tert-butyl 2-{2-[4-(methoxycarbonyl)phenyl]ethyl}-2-propionyl hydrazinecarboxylate To a solution of intermediate 1.2 (564 mg, 1.92 mmol) in pyridine (10 mL) was added propionyl chloride (168 μL, 1.92 mmol) and the reaction mixture was stirred for 18 hrs. The pyridine was removed in vacuo and diluted with EtOAc, washed with brine. The organic solution was dried over sodium sulfate, concentrate in vacuo and purified by flash chromatography using hexane/EtOAc (2:1) to afford the title compound (500 mg, 74% yield) as orange color oil. $R_f$ 0.85 (EtOAc/Hexane 1:1); $^1$H NM (CDCl$_3$) δ 1.04 (t, J=7.32 Hz, 3H), 1.41 (s, 9H), 2.29 (m, 2H), 2.90 (m, 4H), 3.85 (s, 3H), 6.97 (s, 1H) 7.23 (d, J=8.04 Hz, 2H), 7.90 (d, J=8.04 Hz, 2H); MS(m/z) 373.2 (M+Na).

Intermediate 5.2: methyl 4-[2-(1-propionylhydrazino)ethyl]benzoate

To a solution of crude intermediate 5.1 (500 mg, 1.42 mmol) in MeOH (2 mL) was added HCl (6.0 mL, 4M HCl in dioxane) and the mixture was stirred at room temperature for 1 hour. The solvent was then removed in vacuo to afford the title compound (450 mg) as colorless oil (5.2) used in the next step without further purification; MS (m/z): 251.4 (M+1).

Intermediate 5.3: methyl 4-[2-(2-{3-oxo-4-[3-(trifluoromethyl)phenyl]butyl}-1-propionylhydrazino)ethyl]benzoate To a solution of intermediate 5.2 (440 mg, 1.42 mmol) in EtOH (10 mL) was added triethyl amine (562 μL, 4 mmol) and intermediate 4.2 (1.0 g, 4 mmol) and the reaction mixture was refluxed for 3 hours. The solvent was then removed in vacuo and the crude was diluted with EtOAc. The organic solution was washed with brine, dried over sodium sulfate, concentrated and purified by flash chromatography using EtOAC/hexane (1:1) to afford the title compound (232 mg, yield 35%) (5.3) as colorless oil; $R_f$ 0.2 (EtOAc/Hexane 1:1); MS(m/z) 487.3 (M+Na).

Intermediate 5.4: methyl 4-[2-(2-{3-hydroxy-4-[3-trifluoromethyl)phenyl]butyl}-1-propionylhydrazino)ethyl]benzoate To a solution of intermediate 5.3 (232 mg, 0.5 mmol) in MeOH (5 mL) and water (2 mL) was added CeCl$_3$.7H$_2$O (186 mg, 5 mmol) followed by NaBH$_4$ (28 mg, 0.75 mmol) at 0° C. After 15 minutes the solvent was removed and the crude was diluted with EtOAc. The organic solution was washed with brine, dried over sodium sulfate, concentrated to afford the title compound (5.4) (238 mg) used in the next step without further purification; MS (m/z): 489 (M+Na).

To a solution of intermediate 5.4 (238 mg, 0.5 mmol) in THF (3 mL), MeOH (3 mL) and water (1 mL) was added NaOH (200 mg, 5 mmol) and the resulting solution was stirred at RT for 18 hrs. The solvent was removed in vacuo and the crude mixture was diluted in water and purified by RP-HPLC using ACN/H$_2$O to afford the title compound (5) (170 mg, 75% yield) as sodium salt; M/S (m/z): 453.3 (M+1), $^1$H NMR (MeOD) δ 1.05 (t, 3H), 1.45-1.60 (m, 2H), 2.45 (q, 2H), 2.20 (s, 3H), 2.80-3.13 (m, 6H), 3.75 (m, 2H), 3.9-4.0 (m, 1H), 7.30 (d, J=8.04 Hz, 2H), 7.45-7.55 (m, 4H), 7.95 (d, J=8.04 Hz, 2H).

Example 6

4-[2-(2-{3-hydroxy-4-[3-(trifluoromethyl)phenyl]butyl}-1-isobutyryl hydrazino)ethyl]benzoic acid (6)

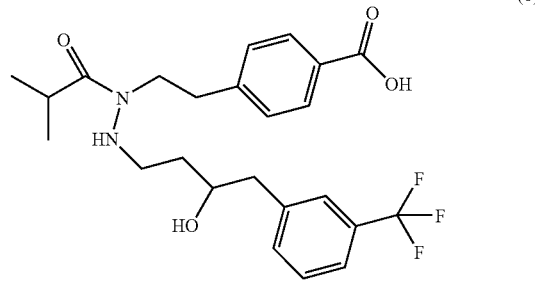

Intermediate 6.1: tert-butyl 2-isobutyryl-2-{2-[4-(methoxycarbonyl)phenyl]ethyl}hydrazinecarboxylate Intermediate 6.1 was prepared from isobutyryl chloride and intermediate 2.1 in a manner analogue to the method of intermediate 5.1.

Example 6: the title was prepared from the appropriate starting materials in a manner analogues to the method of Example 5; M/S (m/z): 467 (M+1); $^1$H NMR (MeOD) δ 0.58 (d, 3H), 0.85 (m, 3H), 1.45-1.60 (m, 2H), 2.20 (m, mH), 2.80-2.90 (m, 6H), 3.20 (m, 1H), 3.60 (m, 1H), 3.75 (m, 1H), 3.9-4.0 (m, 1H), 7.30 (d, J=8.04 Hz, 2H), 7.45-7.55 (m, 4H), 7.95 (d, J=8.04 Hz, 2H).

Example 7

4-[2-(1-acetyl-2-{3-hydroxy-4-[3-(phenylethynyl)phenyl]butyl}hydrazino)ethyl]benzoic acid (7)

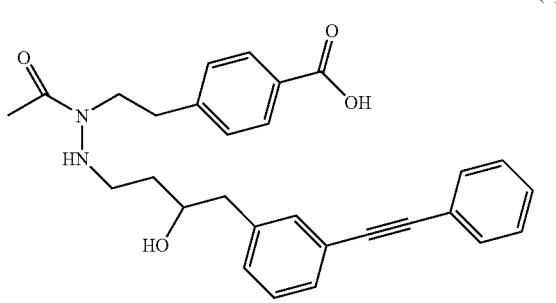

Intermediate 7.1: N-methoxy-N-methyl-2-[3-(phenylethynyl)phenyl]acetamide

To a mixture of [3-(phenylethynyl)phenyl]acetic acid (obtained from (3-iodophenyl)acetic acid, commercially available from Lancaster, and ethynylbenzene as described in *Tetrahedron* 1995, 51, 12645-12660) (6 g, 0.0254 mol), TBTU (16.5 g, 0.0508 mol) and DIEA (27 ml, 0.152 mol) in dry acetonitrile under nitrogen was added N,O-Dimethylhydroxylamine hydrochloride (5 g, 0.0508 mol), commercially available from Aldrich, in portions. The reaction mixture was stirred at room temperature for 24 h and then evaporated to a residue. The residue was diluted with ethyl acetate (400 ml), washed with 2N HCl (250 ml), 10% sodium bicarbonate solution (250 ml×2), water and brine. The solvent was then dried and evaporated to a reside and the residue was purified by chromatography using pet/chloroform (9:1) as eluent to afford (6 g, 85%) the title compound (7.1) as a liquid; $R_f$=0.5 (100% chloroform).

Intermediate 7.2:
1-[3-(phenylethynyl)phenyl]but-3-en-2-one

Intermediate 7.2 was prepared from intermediate 7.1 and vinyl magnesium bromide in a similar method described for intermediate 4.2; $R_f$ 0.75 (hexane/EtOAC3:1) (7.2 and used in the next step without further purification.

Example 7

4-[2-(1-acetyl-2-{3-hydroxy-4-[3-(phenylethynyl)phenyl]butyl}hydrazino)ethyl]benzoic acid The title compound was prepared using the procedure similar to the one used for Example 4 using intermediate 7.2 and intermediate 1.4. MS (m/z): 471.2 (M+H), $^1$H NMR ($D_2O$) δ 1.15-1.50 (m, 2H), 1.90 (s, 3H), 2.40-2.75 (m, 6H), 3.20 (m, 1H), 3.50 (m, 1H), 3.68-3.80 (m, 1H), 7.00-4.40 (m, 9H), 7.45 (m, 2H), 7.70 (m, 2H).

Example 8

4-(2-{1-acetyl-2-[4-(1,1'-biphenyl-3-yl)-3-hydroxybutyl]hydrazino}ethyl)benzoic acid (8)

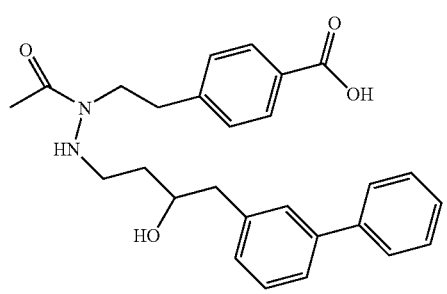

The title compound was prepared using the same methodology described for Example 7 using 1,1'-biphenyl-3-ylacetic acid (commercially available from Aldrich corp.) and intermediate 1.4. MS (m/z): 447.1 (M+H), $^1$H NMR ($D_2O$) δ 1.15-1.50 (m, 2H), 1.90 (s, 3H), 2.40-2.75 (m, 6H), 3.20 (m, 1H), 3.50 (m, 1H), 3.68-3.80 (m, 1H), 7.00-7.40 (m, 9H), 7.45 (m, 2H), 7.70 (m, 2H).

Example 9

4-(2-{1-acetyl-2-[4-(3-bromophenyl)-3-hydroxybutyl]hydrazino}ethyl) benzoic acid (9)

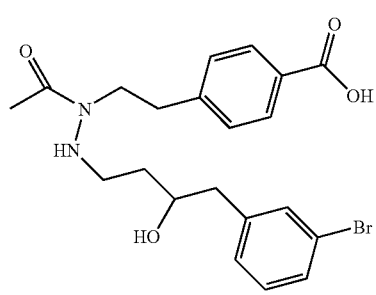

The title compound was prepared from 3-bromophenyl acetic acid, commercially available from Lancaster in a manner analogue to the method of Example 4. MS (m/z): 449.1, 451.0, $^1$H NMR ($D_2O$) δ 1.45-1.60 (m, 2H), 2.04 (s, 3H), 2.70-2.9 (m, 4H), 3.68 (m, 2H), 3.9-4.0 (m, 1H), 7.30 (m, 4H), 7.4 (m, 2H), 7.80 (d, 2H).

Example 10

4-(2-{1-acetyl-2-[3-hydroxy-4-(3-iodophenyl)butyl]hydrazino}ethyl)benzoic acid (10)

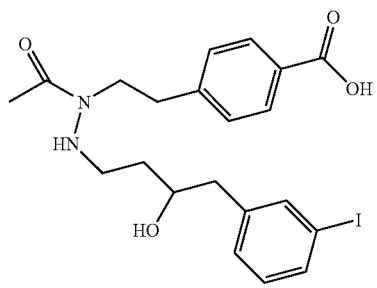

The title compound was prepared from 3-iodophenyl acetic acid, commercially available from Lancaster, in a manner analogue to the method of Example 4. MS (m/z): 497.0 (M+H), $^1$H NMR ($D_2O$) δ 1.45-1.60 (m, 2H), 2.02 (s, 3H), 2.64-2.9 (m, 4H), 3.57-3.62 (m, 2H), 3.57-3.61 (m, 1H), 7.07 (m, 1H), 7.21-7.24 (m, 3H), 7.60 (m, 2H), 7.76 (d, 2H).

Example 11

4-(2-{1-acetyl-2-[4-(3-chlorophenyl)-3-hydroxybutyl]hydrazino}ethyl) benzoic acid (11)

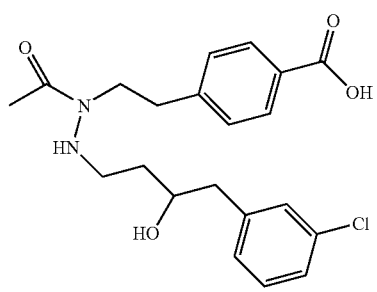

The title compound was prepared from 3-chlorophenyl acetic acid, commercially available from Acros, in a manner analogue to the method of Example 4. MS (m/z): 405.1 (M+H), $^1$H NMR ($D_2O$) δ 1.45-1.60 (m, 2H), 2.02 (s, 3H), 2.64-2.9 (m, 4H), 3.57-3.62 (m, 2H), 3.57-3.61 (m, 1H), 7.10 (m, 1H), 7.21-7.30 (m, 5H), 7.76 (d, 2H).

Example 12

4-{2-[1-acetyl-2-(3-cyclohoxyl-3-hydroxypropyl)hydrazino]ethyl}benzoic acid (12)

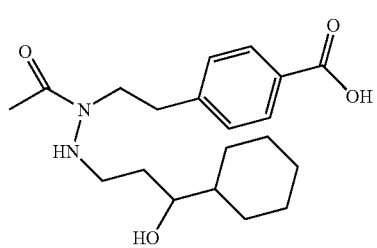

The title compound was prepared from cyclohexane carboxylic acid in a manner analogue to the method of Example 4. MS (m/z): 363.1 (M+H), $^1$H NMR (MeOD) δ 0.95-1.28 (m, 7H), 1.45-1.60 (m, 2H), 1.6-1.85 (m, 4H), 2.02 (s, 3H), 2.80-2.9 (m, 4H), 3.57-3.75 (m, 2H), 7.30 (d, 2H), 7.90 (d, 2H).

Example 13

4-{2-[1-acetyl-2-(3-hydroxy-4-phenylbutyl)hydrazino]ethyl}benzoic acid

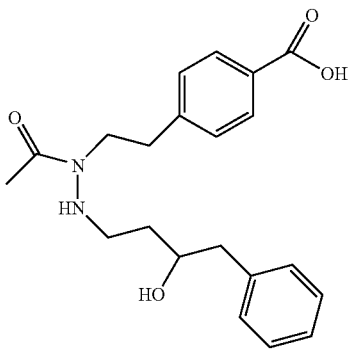

(13)

The title compound was prepared from phenyl acetic acid in a manner analogue to the method of Example 4. MS(m/z): 371.1 (M+H), $^1$H NMR (D$_2$O) δ 1.43-1.60 (m, 2H), 1.55 (s, 1.5H) and 2.0 (s, 1.5H), 2.66-2.91 (m, 6H), 3.61-3.62 (t, 1H), 3.66-3.69 (t, 2H), 3.80-3.92 (m, 1H), 7.21-7.31 (m, 7H), 7.73-7.76 (d, 2H, J=8.04 Hz).

Example 14

4-(2-{1-acetyl-2-[4-(4-chlorophenyl)-3-hydroxybutyl]hydrazino}ethyl) benzoic acid

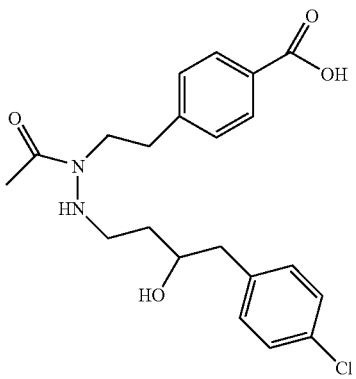

(14)

The title compound was prepared from 4-chlorophenylacetic acid, commercially available from Acros, in a manner analogue to the method of Example 4. MS(m/z): 405.1 (M+H), $^1$H NMR (D$_2$O) δ 1.39-1.60 (m, 2H), 1.55 (s, 1.5H) and 2.0 (s, 1.5H, 2.60-2.91 (m, 6H), 3.58-3.67 (t, 2H), 3.72-3.90 (t, 1H), 3.80-3.92 (m, 1H), 7.10-7.29 (m, 6H), 7.73-7.76 (d, 2H, J=8.04 Hz).

Example 15

4-(2-{1-acetyl-2-[4-(4-fluorophenyl)-3-hydroxybutyl]hydrazino}ethyl) benzoic acid

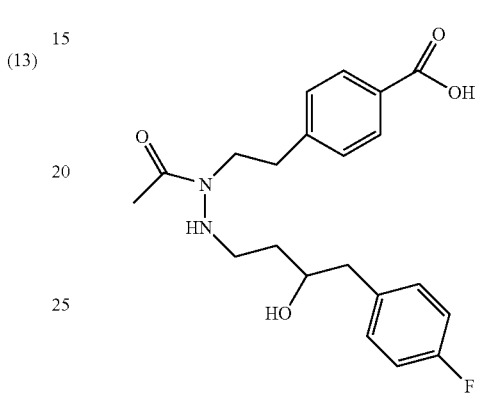

(15)

The title compound was prepared from 4-fluorophenylacetic acid, commercially available from Acros, in a manner analogue to the method of Example 4. MS(m/z): 389.1 (M+H), $^1$H NMR (D$_2$O) δ 1.39-1.60 (m, 2H), 1.55 (s, 1.5H) and 2.0 (s, 1.5H), 2.60-2.91 (m, 6H), 3.58-3.67 (t, 2H), 3.72-3.90 (t, 1H), 3.80-3.92 (m, 1H), 7.10-7.29 (m, 6H), 7.73-7.76 (d, 2H, J=8.04 Hz).

Example 16

4-(2-{1-acetyl-2-[4-(3ethynylphenyl)-3-hydroxybutyl]hydrazino}ethyl) benzoic acid

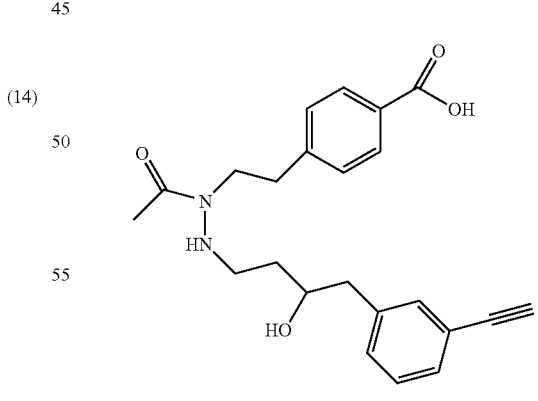

(16)

The title compound was prepared from N-methoxy-N-methyl-2-{3-[(trimethylsilyl)ethynyl]phenyl}acetamide (obtained from 2-(3-iodophenyl) acetic acid and (trimethylsilyl) acetylene as described in *Tetrahedron* 1995, 51, 12645-12660) in a manner analogue to the method of Example 4. The trimethylsilyl group was removed prior to the saponification using Bu$_4$N$^+$F$^-$ in THF, MS(m/z): 395.1 (M+1).

Example 17

4-(2-{1-acetyl-2-[4-(3-fluorophenyl)-3-hydroxybutyl]hydrazino}ethyl) benzoic acid

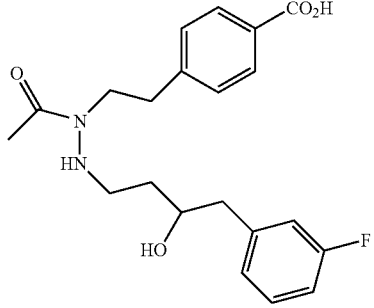
(17)

The title compound was prepared from 3-flurophenylacetic acid in a manner analogue to the method of Example 4. MS(m/z): 389.2 (M+H).

Example 18

4-[2-(1-acetyl-2-{3-hydroxy-4-[4-(phenylethynyl)phenyl]butyl}hydrazino) ethyl]benzoic acid

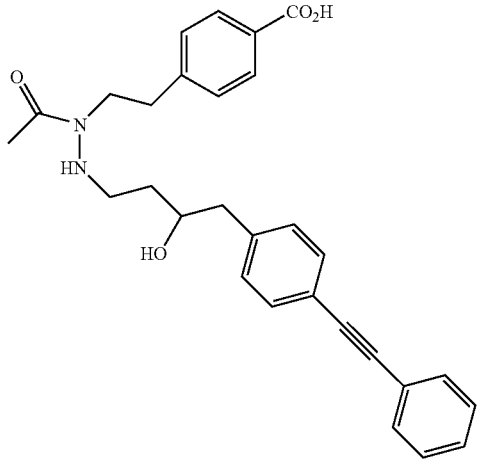
(18)

The title compound was prepared from V-methoxy-N-methyl-2-[4-(phenylethynyl)phenyl]acetamide (obtained from 2-(4-iodophenyl)acetic acid and phenylacetylene as described in *Tetrahedron* 1995, 51, 12645-12660) in a manner analogue to the method of Example 4. MS(m/z): 471.2 (M+H).

Example 19

4-{2-[1-acetyl-2-(3-hydroxy-4-thien-2-ylbuyl)hydrazino]ethyl}benzoic acid

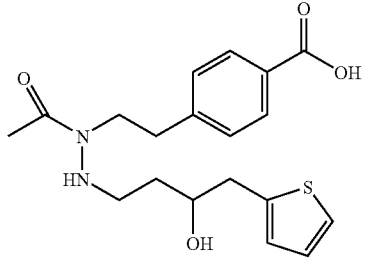
(19)

The title compound was prepared from 2-thiopheneacetic acid, commercially available from Aldrich, in a manner analogue to the method of Example 4. MS(m/z): 377.1 (M+H).

Example 20

4-[2-(1-acetyl-2-{4-[3-cyclopropylethynyl)phenyl]-3hydroxybutyl}hydrazino)ethyl]benzoic acid

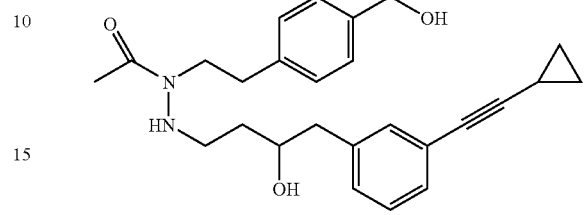
(20)

The title compound was prepared from 2-[3-(cyclopropylethynyl)phenyl]-N-methoxy-N-methylacetamide (obtained from 2-(3-iodophenyl) acetic acid and cyclopropyl acetylene as described in *Tetrahedron* 1995, 51, 12645-12660) in a manner analogue to the method of Example 4. MS(m/z): 435.2 (M+H).

Example 21

Preparation of a Pharmaceutical Formulation

The following Formulation examples illustrate representative pharmaceutical compositions according to the present invention being.

Formulation 1—Tablets

A hydrazide derivative of Formula I is admixed as a dry powder with a dry gelatin binder in an approximate 1:2 weight ration. A minor amount of magnesium stearate is added as a lubricant. The mixture is formed into 240-270 mg tablets (80-90 mg of active amino compound per tablet) in a tablet press.

Formulation 2—Capsules

A hydrazide derivative of Formula I is admixed as a dry powder with a starch diluent in an approximate 1:1 weight ratio. The mixture is filled into 250 mg capsules (125 mg of active amino compound per capsule).

Formulation 3—Liquid

An hydrazide derivative of Formula 1 (1250 mg), sucrose (1.75 g) and xanthan gum (4 mg) are blended, passed through a No. 10 mesh U.S. sieve, and then mixed with a previously prepared solution of microcrystalline cellulose and sodium carboxymethyl cellulose (11:89, 50 mg) in water. Sodium benzoate (10 mg), flavor, and color are diluted with water and added with stirring. Sufficient water is then added to produce a total volume of 5 mL.

Formulation 4—Tablets

A hydrazide derivative of Formula I is admixed as a dry powder with a dry gelatin binder in an approximate 1:2 weight ratio. A minor amount of magnesium stearate is added as a lubricant. The mixture is formed into 450-900 mg tablets (150-300 mg of active amino compound) in a tablet press.

Formulation 5—Injection

A hydrazide derivative of Formula I is dissolved in a buffered sterile saline injectable aqueous medium to a concentration of approximately 5 mg/ml.

Example 22

Prostaglandin EP2 Binding Assay

Compounds of the invention were tested in an EP2 receptor binding assay of the following protocol. As referred to herein, the term an "EP2 receptor binding assay" designates the following protocol.

A mixture containing 20 µg of EP2 receptor membranes, 0.5 mg of wheat germ agglutinin coated PVT-SPA beads, with or without compound of the invention (25 µl per well) or 10 µM of cold PGE2 at 1% DMSO and 20 nM $^3$H-PGE2 in assay buffer containing 25 mM MES, 10 mM MgCl$_2$, 1 mM EDTA, pH 6.0 are incubated in Corning 3600 plates on a plate shaker for 2 hrs at room temperature. $^3$H-PGE2 binding is evaluated by counting the plates on the top count using the $^3$H SPA dpm2 program. The percentage of binding and Ki value for inhibitors are calculated based on the one site competition parameter using the Graphpad® prism program. EP2 Ki values are set forth in the Table I which follows Example 25 below.

Example 23

EP2 cAMP Assay

It is known that PGE2 has a marked effect on cAMP (Cyclic adenosine monophosphate) levels (Coleman et al., 1989). This effect is thought to be achieved via EP2 and EP4 receptors (Choung et al. 1998).

Bone resorption properties of PGE2 is thought to result from a mechanism involving cAMP (Miyaura, 2001). In addition, the actions of gonadotrophins on the ovary and ovarian cyclicity (initiation of follicular development, selection of a single pre-ovulatory follicle, corpus luteum function, corpus luteum regression, and corpus luteum rescue during early pregnancy) are though to be controlled by cAMP.

Therefore, the compounds of the invention are tested for their ability in modulating cAMP levels in cells over-expressing EP2 or EP4 (Example 25 below) receptors.

Compounds of the invention are tested in a total cAMP assay as follows. HEK293-EBNA cells transfected with pCEP4-hEP2 receptors are seeded in 96 well opaque plate (Costar #3917) at 4×10$^4$ cells per well in 100 µl of culture medium (D-MEM/F12 supplemented with 10% FBS, 2 nM L-glutamine, and 250 µg/ml of hygromycin; all from Gibco BRL) and incubated at 37° C. After overnight incubation, the medium is removed from each well and replaced with 45 µl of assay medium consisted of phenol red free D-MEM/F-12, 0.1% BSA (Gibco BRL) and 0.1 mM 3-isobutyl-1-methylxanthine (Sigma). After 15 minutes of incubation at 37° C., 16-16-dimethyl PGE-2 or compounds at desired concentrations in 20 µl of assay medium are added to cells and further incubated at 37° C. for 1 hour. Total cAMP (intra- and extracellular) is measured by using a cAMP-screen ELISA System (Tropix, #CS1000). EC$_{50}$ values are set forth in the Table II which follows Example 25 below.

Example 24

EP4 Binding Assay

Compounds of the invention were tested in an EP4 receptor binding assay of the following protocol.

A mixture containing 20 µg of EP4 receptor membranes, 0.5 mg of wheat germ agglutinin coated PVT-SPA beads, with or without compounds of the invention (25 µl per well) or 10 µM of cold PGE2 at 1% DMSO and 20 nM $^3$H-PGE2 in assay buffer containing 25 mM MES, 10 mM MgCl$_2$, 1 mM EDTA, pH 6.0 are incubated in Corning 3600 plates on a plate shaker for 2 hrs at room temperature. $^3$H-PGE2 binding is evaluated by counting the plates on the top count using the $^3$H SPA dpm2 program. The percentage of binding and Ki value for inhibitors are calculated based on the one site competition parameter using the Graphpad® prism program. EP4 Ki values are set forth in the Table I which follows Example 25 below.

Example 25

EP4 cAMP Assay

Compounds of the invention are tested in a total cAMP assay as follows. HEK293-EBNA cells transfected with pCFP4-hEP4 receptors are seeded in 96 well opaque plate (Costar #3917) at 4×10$^4$ cells per well in 100 µl of culture medium (D-MEM/F12 supplemented with 10% FBS, 2 nM L-glutamine, and 250 µg/ml of hygromycin; all from Gibco BRL) and incubated at 37° C. After overnight incubation, the medium is removed from each well and replaced with 45 µl of assay medium consisted of phenol red free D-MEM/F-12, 0.1% BSA (Gibco BRL) and 0.1 mM 3-isobutyl-1-methylxanthine (Sigma). After 15 minutes of incubation at 37° C., 16-16-dimethyl PGE-2 or compounds at desired concentrations in 20 µl of assay medium are added to cells and further incubated at 37° C. for 1 hour. Total cAMP (intra- and extracellular) is measured by using a cAMP-screen ELISA System (Tropix, #CS1000). EC$_{50}$ values are set forth in the Table III which follows below.

Results of the assays of Examples 22 and 24 are set forth in the following Table I, of Example 23 in Table II and of Example 25 in Table III below, respectively wherein the tested compound is identified by the corresponding synthetic Example number.

TABLE I

| Example Number | h-EP2 Ki (µM) | h-EP4 Ki (µM) |
|---|---|---|
| 2 | 32.9 | 0.4 |
| 4 | 4.45 | 0.53 |
| 6 | N.A. | 0.332 |
| 7 | 4.21 | 0.045 |
| 8 | N.A. | 0.115 |
| 9 | N.A. | 0.149 |
| 10 | N.A. | 0.097 |
| 16 | N.A. | 0.131 |

TABLE II

| Example Number | h-EP2 EC$_{50}$(µM) |
|---|---|
| 2 | 6.03 |

TABLE III

| Example Number | h-EP4 EC$_{50}$(µM) |
|---|---|
| 4 | 0.0004 |
| 7 | 0.00015 |

Example 26

In Vivo Ovulation Assay

Ovulation induction activity of compounds of the invention may be tested in a mature mouse ovulation induction model.

Mature 10-week-old CD-mice are used. Reagents are prepared as follows: PMSG (pregnant mare serum gonadotropin) (Calbiochem, cat #367222) and hCG (Serono) are diluted in PBS. PGE2 (Cayman, Ann Arbor Mich.) is dissolved in ethanol and diluted with 0.154 M NaHCO2 Buffer (pH 8.0) to final concentration of ethanol of less than 3 percent. A compound of the invention (based on solubility) is pre-dissolved in ethanol, DMSO or other reagents. The compounds of the invention are then diluted with saline or other diluents such as PBS or NP3S (5% N-methyl-pyrrolidinone/30% PEG400/25% PEG200/20% Propylene Glycol in saline). PMSG stimulates ovarian follicular development. After PMSG stimulation, the mature follicules can be stimulated to rupture and release oocytes by an ovulation trigger, such as hCG or a compound of the invention.

The following test protocol is employed for the test animals (typically 5 animals per test group).
Day 1: Inject 5 IU PMSG in 200 μl PBS (i.p. 15:00 PM)
Day 2: No administration
Day 3: Injection of ovulation trigger hCG (i.p.) or hCG replacement (PGE2 or compound of the invention, s.c., i.v. or oral route), 15:00 PM
Day 4: Eighteen hours after injections of the ovulation triggers, animals are sacrificed by $CO_2$ asphyxiation and abdominal cavities are opened using fine scissors and forceps. Uterus, oviducts and ovaries are collected and placed in pre-labeled dishes containing phosphate buffered saline (PBS). The collected tissues are transferred to the laboratory and intact oviduct carefully dissected out from uterus and ovary under the dissection microscope. The dissected oviducts are placed on the glass microscopic slide and covered with another slide. Two slides are taped on two edges. The numbers of ovulated ova in the oviducts are counted using upright microscope with 4× objective and recorded.

For evaluating the oral activity of this compound, two experiments are conducted, the first experiment is conducted with non-fasted animals and the second experiment is conducted in 24 h fasted animals (water provided). Compounds of the invention, based on their solubility, are pre-dissolved in ethanol, DMSO or other reagents. Compounds of the invention are then with saline or other diluents such as PBS or NP3S before oral administration (i.e. 5% N-methyl-pyrrolidinone/30% PEG400/25% PEG200/20% Propylene Glycol in saline.

Compounds of the invention are submitted to testing in the in vivo ovulation induction model as described above in order to assess their ability to induce ovulation via subcutaneous (s.c.), oral (p.o.) and intravenous (i.v.) routes of administration.

Example 27

In Vivo Inhibition of Guinea Pig Broncho-constriction

The activity of compounds of the invention in dilation of bronchiolar muscles, may be tested in different models. Guinea pig pulmonary—cholinergic in vivo model is generally used to test the materials for the treatments of asthma in human (Fleisch et al., 1985) Compounds of the invention can be tested in this methacholine-induced bronchomuscle constriction model as described below.

Groups of 3 Duncan Hartley derived male or female guinea pigs weighing 250±50 g are anesthetized with pentobarbital sodium (50 mg/kg i.p., plus an additional 15 mg/kg i.p. if required) and succinylcholine chloride (2 mg/animal i.p.) is subsequently administered to prevent spontaneous respiration. Body temperature is maintained at 37° to 38° C.

The trachea is cannulated and the guinea pig is ventilated with a Harvard rodent respirator in a closed system. Tracheal pressure is recorded through a side-arm of the cannula connected to a P23ID Statham transducer. Respiratory rate is set at 50 strokes/minute with a stroke volume (approximately 1 ml/100 g) sufficient to produce a baseline tracheal pressure of 6 cm $H_2O$. Mean arterial pressure (BP) is monitored from a cannulated carotid artery, and heart rate (HR) is obtained from chest electrodes arranged for lead II. The jugular vein is cannulated for i.v. vehicle or drug administration in a volume of 1 ml/kg.

Cholinergic-induced bronchoconstrictor responses, reflected as increases in tracheal pressure (cm $H_2O$), are elicited by administration of methacholine hydrochloride (10 μg/kg base weight i.v.). In vehicle-treated control animals, methacholine-induced bronchoconstriction ranges from 70 to 90 percent of its own maximum response (about 40 to 65 percent of maximum possible bronchoconstriction obtained by tracheal occlusion).

Compounds of the invention are also tested via intratracheal (IT) route of administration. In this other experiment, compound of the invention, reference compound or vehicle is administered IT 10 (5 min for experiment 1 and 2) minutes before methacholine chloride (10 μg/kg i.v.) induced bronchoconstriction. Tracheal pressure (ITP), blood pressure and heart rate are measured immediately as indicated in the material and methods sections.

MED (medium effective dose) is measure. A 50 percent or greater ($\geqq$50%) inhibition of the induced broncho-constriction relative to vehicle treated control animals is considered significant.

Compounds of the invention are administered i.v. (10 mg/kg) 5 minutes before the methacholine challenge in 3 guinea pigs. A percent or more ($\geqq$50) inhibition of the induced broncho-constriction relative to vehicle treated control animals is considered significant.

Example 28

In Vivo Inhibition of LPS-induced TNFα Release in Mice

Prostaglandin EP2 is suggested to be an endogenous inhibitor of inflammation through the EP4 receptor. Therefore EP2 and/or EP4 agonists are supposed to have an anti-inflammatory activity.

Endotoxins are the lipopolysaccharides (LPS) constituents of the outer membrane of Gram negative bacteria. Response to LPS has been shown to involve the activation of different cell populations and to lead to the expression of various inflammatory cytokines that include tumor necrosis factor-alpha (TNFα) and interferon gamma (IFN-γ).

The anti-inflammatory activity of compounds of the invention may be assessed after a LPS challenge using the following protocol:

Eight weeks old C3H/HEN mice (IFFA-CREDO, L'arbresle, France) receive an oral treatment with compounds of the invention 6 different doses (0.001, 0.01, 0.1, 1 or 3 and 10 mg/kg in 0.5% CMC/0.25% tween-20). Six mice are used by group. Fifteen minutes later, endotoxins (O111:B4 Sigma, 0.3 mg/kg) are intraperitoneally injected. Heparinized whole blood is collected by decapitation. TNFα level is determined in plasma by ELISA (R & D Systems, Abdingdon, UK). Control animals receive 0.5% CMC/0.25% tween-20 (10 ml/kg) as vehicle. Data obtained from experiments are expressed as the mean±SEM and analysed using one-way analysis of variance (ANOVA) followed by Dunnett's t-test.

The activity of the compounds of the invention is expressed as a percentage of inhibition of TNF release and the Inhibitory Dose at 50% of the maximum effect ($ID_{50}$) is calculated in mg/kg.

Example 29

In Vivo Effect on Penile Corpus Cavernosum Tissue Relaxation

Penile erection is based on three main physiological events: an increase in the arterial blood flow, a relaxation of the expansive tissue of the corpora carvernosa and the corpus spongiosum, and an obstruction of the venous return by mechanical compression of the veins caused by the expansive tissue.

PGE1 is used in the treatment of erectile dysfunction to relax smooth muscle and therefore to promote the development of erection. The administration of PGE1 is performed by local injection into the cavernous tissue of the penis. However, PGE1 has a low selectivity for prostanoid receptors and has irritant effects. Selective agonists EP2 and/or EP4 have been developed for the treatment of erectile dysfunction (WO 99/02164)

The effect of compounds of the invention on the relaxation of penile corpus cavernosal tissue strips may be assayed for example in an assay on human or rabbit tissue as described below:

Human tissue procurement. Cavernosal tissue is obtained from patients undergoing penile prosthesis implantation surgery for treatment of erectile dysfunction. In the operating room, biopsies of the corpora cavernosa are immediately placed in chilled (4° C.) physiologic salt solution and transported to the laboratory. Tissue strips, measuring approximately 3 mm×3 mm×10 mm, are cut and prepared for organ bath studies.

Rabbit tissue procurement. Adult male New Zealand White rabbits (4.5-5.0 kg) are sedated with ketamine (35 mg/kg) and xylazine (5 mg/kg) and euthanized with sodium pentobarbital (60 mg/kg body weight). Following exsanguination, the penis is excised and cleaned by removing the corpus spongiosum and urethra. Corpus cavernosum tissue strips are dissected away from the surrounding tunica albuginea and prepared for organ bath studies.

Preparation of compound stock solutions and dose responses. $PGE_1$ (Cayman Chemical Co., Ann Arbor, Mich.) is stored at −20° C. in solid form until the day of use. Stock solutions are made by adding 1 ml of 70% DMSO to a vial containing 1 mg of $PGE_1$. Compounds of the invention are dissolved in 1 ml of 70% DMSO, divided into 100 µl aliquots and stored at −20° C. until use. For dose responses in organ baths, stock solutions of $PGE_1$ and compounds of the invention are diluted with 70% DMSO to make the highest concentration and then serially diluted with 2% DMSO for all other doses. In a typical dose response curve, the concentration of DMSO is checked to remain below 0.1% in the 25 ml bath and to not exceed 0.5% at the highest dose.

Organ bath studies. Human or rabbit cavernosal tissue strips are mounted onto a fixed support with silk ties and attached to a tension transducer (model FT03; Grass-Telefactor, Astro-Med, Inc. West Warwick, R.I.) with a rigid metal wire. After mounting, tissue strips are immersed in 25 ml baths of physiologic salt solution (PSS; 118.3 mM NaCl, 4.7 mM KCl, 0.6 mM $MgSO_4$, 1.2 mM $KH_2PO_4$, 2.5 mM $CaCl_2$, 25 mM $NaHCO_3$, 0.026 mM $CaNa_2EDTA$, 11.1 mM glucose). The solution is gassed with 95% air/5% $CO_2$ to attain a pH of 7.4 and the temperature is maintained at 37° C. All tissue strips are treated with 3 µM indomethacin to inhibit endogenous prostanoid production and minimize spontaneous contractile activity. The corpus cavernosum tissue is stretched incrementally and the optimal resting isometric tension for contraction is determined. After every 3-4 stretches (1 g tension/stretch), the tissue is contracted with 1 µM phenylephrine. When the amplitude of the phenylephrine-induced contraction is within 10% of the previous contraction, that tension is considered optimal for isometric contraction. All tissue strips are extensively washed with fresh PSS. Tissue strips are then contracted with 1 µM phenylephrine. After stable tone is achieved, tissue strips are exposed to increasing concentrations of $PGE_1$ or compounds of the invention.

Data analysis. At the end of each experiment, all tissue strips are treated with 10 µM papaverine and 10 µM nitroprusside to induce maximal relaxation (100%). The total amount of relaxatory response over the range of drug concentrations tested is determined by the area under the plotted curves. $EC_{50}$ values are calculated using Prism software (GraphPad, San Diego, Calif.). For final analysis of data, relaxation parameters are compared using ANOVA. If the ANOVA p-value is less than 0.05, paired post-test comparisons is carried out using the Tukey-Kramer test.

Example 30

In Vivo Effect on Bone Loss Prevention

The activity of compounds of the invention as a bone anabolic agent can be tested for example in a rat ovariectomy model such as follows.

Virgin female Sprague Dawley rats Rats are randomized into treatment groups based on pre-dose body weight measurements. The aim is to achieve approximately the same average body weight for every treatment group.

Surgery:

Animals are sedated with Ketamine and Xylazine (SOP ST-AEP007). The hair on the dorsal abdominal surface is shaved and prepped for aseptic surgery. A single incision is made along the midline, starting just anterior to the lumbar region of the spine. The underlying musculature on both sides of the dorso-lateral region of the abdomen is exposed. An incision is made through the musculature to gain access to the abdominal cavity.

For a group of animals ("Ovx"), the ovary is located and cut at the junction of the uterine horn and removed. The uterus is replaced and the muscles sutured. Repeat on the contralateral side.

For a control group of animals ("Sham"), the ovaries are located and exteriorized, but not removed. The uterus and ovaries are replaced into the abdominal cavity and the muscles sutured.

The muscle layers are closed with suture and the skin incision closed using wound clips.

Dosing

Dosing is commenced one day after the surgery is performed. The animals receive daily subcutaneous injections for 6 weeks following surgery. The doses of 0.1, 1.0, 10.0 mg/kg of compounds of the invention are used A control group receives daily subcutaneous injections of 17 β estradiol (Sigma Chemicals) of 30 μg/kg for 6 weeks following surgery. Control groups of animal (the "sham" group and an "Ovx" group) are injected s.c. vehicle (saline).

Fluorochrome Labels

To enable the performance of dynamic histomorphometry, two injections of calcein (10 mg/kg, i.p.) are given 6 and 2 days prior to the necropsy.

Body Weights and Clinical Observations

Body weights are recorded weekly, beginning one week prior to the commencement of treatment and continuing until the conclusion of the treatment period. In addition, the rats are observed daily for signs of ill health or reaction to treatment.

Blood and Urine Biochemistry

An eighteen-hour urine specimen is collected from each animal prior to the sacrifice using metabolic cages. At sacrifice, blood samples are collected from each rat, under inhalation anesthesia (ether) from the retro-orbital sinus. Following parameters are measured in urine and serum.

Parameter Method

Urinary deoxypyridinoline is measured by Immuno-assay (Pyrilinks-D Quidel, Mt. View, Calif.); Urinary creatinine is measured by COBAS chemistry instrument (Creatinine Reagent Roche Diagnostics, Indianapolis, Ind.); Serum osteocalcin is measured by Immuno-assay (Rat OSU IRMA, Immunotopics San Clemente, Calif.)

Necropsy:

Upon completion of dosing and urine/blood collection, animals are euthanized using carbon dioxide asphyxiation.

All animals are subjected to the following procedure. Terminal body weights are recorded. A gross examination is performed and a check for abnormalities is performed. The following investigation are performed, as detailed:

Bone Mineral Density Scans: L2-L4 lumbar vertebrae is subjected to DXA (Dual-energy X-ray absorptiometry) scan using a PIXImus instrument (Lunar Corp. Madison, Wis.). Bone mineral content, area and density are determined from the PIXI scan. Bone mineral density measurements by DXA are described in Fornica et al. 1998.

Right femur is subject to pQCT (peripheral quantitative computed tomography) scan using a Stratec XCT RM and associated software (Stratec Medizintechnik Gmbh, Pforzheim, Germany. Software version 5.40 C). The femur is scanned at two sites, 20% of the distal femur and 50% of the mid-femur. The position is verified using scout views and scan results from one 0.5 mm slice perpendicular to the long axis of the femur shaft is recorded. Total bone mineral content, total bone area, total bone mineral density, trabecular bone mineral content, trabecular bone area and trabecular bone mineral density are analyzed from the scan of the distal femur. For the midshaft femur, total bone mineral content, total bone area, total bone mineral density, cortical bone mineral content, cortical bone area, cortical bone mineral density, periosteal perimeter and endosteal perimeter are analyzed. Bone mineral density measurements by pQCT are described in Formica et al., 1998 and in Tsugeno, 2002.

Biomechanical Testing of Lumbar Vertebrae and Femurs:

LS Lumbar vertebra is isolated from L5-L6 and prepared for mechanical testing by removing the vertebral arch and pedicle using a low-speed diamond saw. The cranial and caudal ends of each vertebral body are also removed to produce a vertebral body specimen with two parallel surfaces and a height of approximately 4 mm. The width of the vertebral body in the medial-lateral and anterior-posterior directions is measured using electronic digital calipers. These values are recorded and used in the calculation of cross-sectional area. The height of the vertebral body specimen is also taken with an electronic caliper and recorded. The specimens are then placed between two platens and load applied at a displacement rate of 6 mm/min until failure in an Instron Mechanical Testing Instrument (Instron 4465, retrofitted to 5500).

The load and displacement are recorded by Instron Instrument Software (Merlin II, Instron) and the locations for maximum load at failure, stiffness and energy absorbed are selected manually from the load and displacement curve. The intrinsic properties, stress, elastic modulus and toughness are then calculated from maximum load, stiffness, energy absorbed, cross-sectional area, and height according to the following equations:

After the pQCT scan, the anterior to posterior diameter at the midpoint of the femoral shaft is taken with an electronic caliper and recorded. Femur is then placed on the lower supports of a three point bending fixture with anterior side facing downward in an Instron Mechanical Testing Instrument (Instron 4465, retrofitted to 5500). The span between the two lower supports is set at 14 mm. The upper loading device aligned to the center of the femoral shaft. The load is applied at a constant displacement rate of 6 mm/min until the femur breaks. The locations of maximal load, stiffness and energy absorbed are selected manually and values calculated by instrument's software (Merlin II, Instron). The intrinsic properties, stress, elastic modulus and toughness are calculated from maximum load, stiffness, energy absorbed, anterior-posterior diameter, and moment of inertia.

After the three point bending test, a 3-mm segment of the distal femoral metaphysis is cut directly proximal to the femoral condyle with a low-speed diamond saw. The load is applied with a cylindrical indenter (with a flat testing face of 1.6 mm diameter (d)) to the center of marrow cavity on the distal face of the segment. The indenter is allowed to penetrate the cavity at a constant displacement rate of 6 mm/min to a depth of 2 mm before load reversal. The locations of maximum load, stiffness and energy absorbed is selected manually from load displacement curve and then calculated by the instrument's software (Merlin II, Instron). Stress is calculated by dividing the maximum load by the indenter area.

Bone Histology and Dynamic Histomorphometry:

Dehydration, Embedding and Sectioning

Formalin-fixed samples of proximal tibia are dehydrated in a series of ascending ethanol concentration. Following dehydration, bone samples are infiltrated and embedded in methyl methacrylate-based plastic. Embedded samples of the proximal tibia are sectioned longitudinally using a Leitz motorized rotary microtome equipped with a tungsten-carbide microtome knife. Once the blocks are trimmed, 4 μm sections are stained with Goldner's trichrome stain for microscopy. The 8 μm sections are left unstained for epifluorescence microscopy.

Histomorphometric Determinations

Static and dynamic histomorphometry of the proximal tibia is performed. The measurement includes the secondary spongiosa (area that is 1.05 from the lowest point of the growth plate).

Bone histomorphomctry is performed using an OsteoMeasure software program (OsteoMetrics, Inc. Atlanta, Ga.) interfaced with a Nikon Eclipse E400 light/epifluorescent microscope and video subsystem. Histomorphometry is read in a blinded manner. Total tissue area, trabecular bone area, trabecular bone perimeter, and osteoclast perimeter is measured on 4 µm thick Goldner's trichrome stained sections. Percent trabecular bone area, trabecular number, trabecular thickness, trabecular separation and osteoclast perimeter as a percentage of bone surfaces are then calculated according to standardized formulae. For dynamic parameters, single-labeled calcein perimeter, double-labeled calcein perimeter, and interlabel width (label thickness) is measured on 8 µm thick unstained sections, and the mineralizing surface, mineral apposition rate, bone formation rate-surface referent is calculated.

Statistics

Results are analyzed using analysis of variance (group) using SAS software (SAS Institute, Cory, N.C.). Group comparison is performed using Dunnett's procedure using "Ovx" + vehicle group as reference group. All results are expressed as mean +/−SD.

The invention has been described in detail with reference to preferred embodiments thereof. However, it will be appreciated that those skilled in the art, upon consideration of this disclosure, may make modifications and improvements within the spirit and scope of the invention.

Example 31

In Vivo Inhibition of Tobacco Smoke-induced COPD

The anti-inflammatory activity of compounds of the invention in respiratory diseases such pulmonary inflammation as observed in emphysema and Chronic Obstructive Pulmonary Diseases (COPD) can be tested as follows.

Female A/J mice (5 per exposure chamber) are exposed daily to Tobacco smoke (TS) generated from cigarettes or air for 11 consecutive days. Initial exposure is to 2 cigarettes on day 1 increasing to a maximum of 6 cigarettes by day 6/7. Exposure thereafter to Day 11 is 6 cigarettes. The rate of increase is regulated with regard to the daily observed tolerance of the mice.

Tobacco smoke exposed animals (n=60, 10/group) are orally dosed twice daily (−1 h and +6 h; 5 ml/kg) with either vehicle (methyl cellulose 0.5%) or compounds of the invention at doses at or about 1, 5, 10, 15 and 20 mg/kg.

Air exposed animals (n=10) are treated with vehicle.

Animals are killed by anaesthetic overdose (pentobarbitone Na, 100 mg/kg i.p.) 24 h following the 11$^{th}$ and final TS exposure. Blood is collected by cardiac puncture for preparation of plasma which is stored frozen at −20° C.

Broncho-alveolar lavage (BAL) is performed using 0.4 ml of heparinised phosphate buffered saline (PBS).

Cells recovered from the BAL are used for total and differential cell counts (cytospin preparation). BAL supernatants are frozen for subsequent analysis of protein levels. The remaining BAL fluid is analyzed for KC levels or for mucin.

Groups:
A. Vehicle p.o. twice daily (vehicle 5 ml/kg; −1 h &+6 h)/Air exposure
B. Vehicle p.o. twice daily (vehicle 5 ml/kg; −1 h &+6 h)/TS exposure
C. Compounds of the invention p.o. twice daily (1-20 mg/kg; −1 h &+6 h)/TS exposure The percentage of inhibition induced by compounds of the invention is calculated.

The mean value for the sham controls is substracted from all the TS groups and the new value for the drug group is divided by the new value for the control TS group.

The invention has been described in detail with reference to preferred embodiments thereof. However, it will be appreciated that those skilled in the art, upon consideration of this disclosure, may make modifications and improvements within the spirit and scope of the invention.

Example 32

In Vivo Inhibition of Dextran Sodium Sulfate-induced Colitis

The anti-inflammatory activity of compounds of the invention in colitis can be assayed as follows.

Within 6-10 days after ingesting Dextran Sodium Sulfate (DSS) mice show sign of diarrhea, rectal bleeding and weight loss and colonic mucosal lesions include multiple erosion, ulceration, and marked inflammatory cell infiltration.

Ulcerative colitis (UC) is induced in female mice (Balb/c, 20-22 g, Elevage Janvier) by Dextran Sodium Sulfate (DSS 4%) administered in drinking water. The mice have free access to DSS during 5 days.

The compounds of the invention are solubilized in 0.25% CMC/0.5% Tween 20 and administered by gavage at days 3, 4, 5 and 6 after the induction of the UC.

The Animals are Divided in Three Groups:

The "treated group" wherein the animals have free access to DDS and are treated each day with compounds of the invention.

The "Dextran 4%" group wherein the animals have free access to DDS 4% and 0.5% CMC/O0.25% tween (vehicle) and are not treated.

The "control" group or "sham" group that do not receive DDS 4%.

The Following Parameters were Recorded:

The body weight is determined daily.

The severity of the UC is assessed by a clinical score estimating the constituency of the stool (0=firm, 1=loose, 2=diarrhea) and the presence of blood (0=no blood, 1=occult blood, 2=gross rectal bleeding).

Seven days after the induction of the disease, the animals are sacrificed. The length and the weight of the colon are determined and the ratio Length/Weight/100 g body weight was calculated.

The percentages of inhibition of weight loss, of clinical scores and of increase in the ratio colon length/weight, are calculated as follows:

% inhibition=(1−("value for treated group"−"value for control group"/"value for Dextran 4% group"−"value for control group))*100.

The percentages of inhibition are calculated for each days 5, 6 and 7 for each parameter.

Example 33

In Vivo Inhibition of Aspirin-induced Gastric Ulceration

The activity of compounds of the invention as protective agents against gastric ulceration can be assayed as follows and as described in Guth et al., 1979.

Compounds of the invention are administered p.o. (100 mg/kg) to a group of 3 Wistar derived male or female overnight fasted rats weighing 200±20 g, 60 minutes before oral gavage with aspirin (150 mg/kg).

Four hours later, animals are sacrificed and gastric ulceration is scored for degree of hemorrhage and severity of ulcerative lesions as follows: 0=no hyperemia or bleeding, 1=hyperaemia, 2=slight spot bleeding, 3=hyperemia plus slight spot bleeding, 4=hyperemia plus spot bleeding within entire stomach. Reduction of concurrent control score values by 50 percent or more (≧50%) is considered significant.

REFERENCES

Abramowitz et al. 2000, Biochimica et Biophysica Acta 1483, 285-293;
Benoit et al., 2002, Expert Opinion in Therapeutical Patents, 12 (8)1225-1235;
Choung et al., 1998, Journal of Cellular Biochemistry 71:254:263;
Coleman et al. 1989, Prostanoids and their Receptors. In Comprehensive Medicinal Chemistry, The rational Design, Machanistic Study and Therapeutic Application Of Chemical Compounds vol. 3, Ed Hansch et al., 643-714, Pergamon Press, Oxford, UK;
Coleman et al. 1994, Pharmacological Reviews 46 (2), 205-229;
Fleisch, et al., 1985, K. Pharmacol. Exp. Ther. 233: 148-157;
Formica et al., 1998, Osteoporosis International, 8 (5), 460-467;
Hyman et al., 1999, J Viral Hepat., 6(4):329-36;
Meltzer et al., 1993, J. Med. Chem., 36, 855-862;
Miyaura C., 2001, Nippon Yakuigaku Zasshi 117(4):293-7;
Piancatelli et al., 1997, J. Org. Chem. 62, 6974-6977;
Levi et al., 1998 Biochimie 80(11): 899-904;
Sharpless et al., 1987, J. Am. Chem. Soc. 1987, 109, 5765-5780;
Sharpless et al., 1982, J. Org. Chem. 1982, 47, 1378-1380;
Takayama et al. 2002, The Journal of Biological Chemistry, 277, 46, 44147-44154;
Tsugeno 2002, Osteoporosis International 13(8), 650-656;
Ushikubi et al., 2000, Jpn J Pharmacol 83(4):279-85;
EP 1114816 Ono Pharmaceuticals;
U.S. Pat. No. 6,235,780 Ono Pharmaceuticals;
WO 9933794 Ono Pharmaceuticals;
US 20010056060 Pfizer;
WO 0242268 Pfizer;
WO 0146140 Pfizer;
WO 9902164 Synphora;
WO 0224647 Ono Pharmaceuticals;
US 20020004495 Merck;
WO 0003980 Ono Pharmaceuticals.

The invention claimed is:
1. A hydrazide derivative of Formula (I):

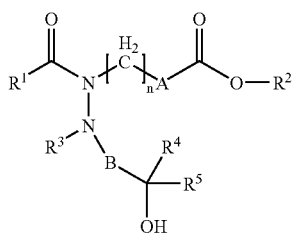

as well as its geometrical isomers, its optically active forms as enantiomers, diastereomers and mixtures of these, as well as salts thereof, wherein:

A is selected from the group consisting of $C_3$-$C_8$ cycloalkyl, heterocycloalkyl, aryl and heteroaryl;
B is selected from the group consisting of $C_1$-$C_6$ alkylene, $C_2$-$C_6$ alkenylene, and $C_2$-$C_6$ alkynylene;
$R^1$ is selected from the group consisting of H, $C_1$-$C_6$ alkyl, $C_2$-$C_6$ alkenyl, $C_2$-$C_6$ alkynyl, $C_3$-$C_8$ cycloalkyl, heterocycloalkyl, aryl $C_1$-$C_6$ alkyl, heteroaryl $C_1$-$C_6$ alkyl, aryl and heteroaryl;
$R^2$ and $R^3$ are independently selected from the group consisting of H, $C_1$-$C_6$ alkyl, $C_2$-$C_6$ alkenyl and $C_2$-$C_6$ alkynyl;
$R^4$ is selected from the group consisting of hydrogen and $C_1$-$C_6$ alkyl;
$R^5$ is selected from the group consisting of hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_3$-$C_8$ cycloalkyl $C_1$-$C_6$ alkyl, aryl $C_1$-$C_6$ alkyl, heteroaryl $C_1$-$C_6$ alkyl, aryl and heteroaryl; and
n is an integer selected from the group consisting of 1, 2, 3, 4, 5 and 6.

2. The hydrazide derivative according to claim 1, wherein A is selected from the group consisting of aryl and heteroaryl.
3. The hydrazide derivative according to claim 1, wherein A is phenyl.
4. The hydrazide derivative according to claim 1, wherein B is ethylene.
5. The hydrazide derivative according to claim 1, wherein $R^1$ is $C_1$-$C_6$ alkyl.
6. The hydrazide derivative according to claim 1, wherein $R^2$ is H.
7. The hydrazide derivative according to claim 1, wherein $R^3$ selected from the group consisting of H and methyl.
8. The hydrazide derivative according to claim 1, Wherein $R^3$ is H.
9. The hydrazide derivative according to claim 1, Wherein $R^4$ is H.
10. The hydrazide according to claim 1, wherein n is 2.
11. The hydrazide derivative according to claim 1, wherein A is phenyl; B is ethylenyl; $R^1$ is $C_1$-$C_6$ alkyl; $R^2$ and $R^4$ are H; $R^3$ is selected from the group consisting of H and methyl; and n is 2.
12. The hydrazide derivative according to claim 1, wherein $R^5$ is selected from the group consisting of H, $C_1$-$C_6$ alkyl and $C_3$-$C_6$ cycloalkyl.
13. The hydrazide derivative according to claim 1, wherein $R^5$ is aryl $C_1$-$C_6$ alkyl.
14. The hydrazide derivative according to claim 1, wherein $R^5$ is heteroaryl $C_1$-$C_6$ alkyl.
15. The hydrazide derivative according to claim 1, wherein $R^5$ is $C_3$-$C_8$ cycloalkyl.
16. The hydrazide derivative according to claim 1, selected from the group consisting of: 4-(2-{1-acetyl-2-[4-(3-chlorophenyl)-3-hydroxybutyl]hydrazino}ethyl)benzoic acid;
4-(2-{1-acetyl-2-[3-hydroxy-4-(3-iodophenyl)butyl] hydrazino}ethyl)benzoic acid;
4-(2-{1-acetyl-2-[4-(3-bromophenyl)-3-hydroxybutyl] hydrazino}ethyl)benzoic acid;
4-(2-{1-acetyl-2-[4-(1,1'-biphenyl-3-yl)-3-hydroxybutyl] hydrazino}ethyl)benzoic acid;
4-[2-(1-acetyl-2-{3-hydroxy-4-[3-(phenylethynyl)phenyl]butyl}hydrazino)ethyl]benzoic acid;
4-{2-[1-acetyl-2-(3-hydroxy-4-phenylbutyl)hydrazino] ethyl}benzoic acid;
4-(2-{1-acetyl-2-[4-(4-chlorophenyl)-3-hydroxybutyl] hydrazino}ethyl)benzoic acid;
4-(2-{1-acetyl-2-[4-(4-fluorophenyl)-3-hydroxybutyl] hydrazino}ethyl)benzoic acid;

4-(2-{1-acetyl-2-[4-(3-ethynylphenyl)-3-hydroxybutyl]hydrazino}ethyl)benzoic acid;
4-(2-{1-acetyl-2-[4-(3-fluorophenyl)-3-hydroxybutyl]hydrazino}ethyl)benzoic acid;
4-[2-(1-acetyl-2-{3-hydroxy-4-[4-(phenylethynyl)phenyl]butyl}hydrazino)ethyl]benzoic acid;
4-{2-[1-acetyl-2-(3-hydroxy-4-thien-2-ylbutyl)hydrazino]ethyl}benzoic acid;
4-[2-(1-acetyl-2-{4-[3-(cyclopropylethynyl)phenyl]-3-hydroxybutylhydrazino)ethyl]benzoic acid;
4-[2-(2-{3-hydroxy-4-[3-(trifluoromethyl)phenyl]butyl}-1-isobutyrylhydrazino)ethyl]benzoic acid;
4-[2-(2-{3-hydroxy-4-[3-(trifluoromethyl)phenyl]butyl}-1-propionylhydrazino)ethyl]benzoic acid;
4-[2-(1-acetyl-2-{3-hydroxy-4-[3-(trifluoromethyl)phenyl]butyl}hydrazino)ethyl]benzoic acid;
4-{2-[1-acetyl-2-(3-cyclohexyl-3-hydroxypropyl)hydrazino]ethyl}benzoic acid; and a pharmaceutically acceptable salt of any of said compounds.

17. A hydrazide derivative selected from the group consisting of:
4-{2-[1-acetyl-2-(3-hydroxyoctyl)hydrazino]ethyl}benzoic acid;
4-{2-[1-acetyl-2-(3-hydroxyoctyl)-2-methylhydrazino]ethyl}benzoic acid;
4-{2-[1-acetyl-2-(3-hydroxybutyl)hydrazino]ethyl}benzoic acid; and a pharmaceutically acceptable salt of any of said compounds.

18. A pharmaceutical composition comprising a pharmaceutically acceptable carrier and one or more compounds according to claim 1.

19. A process for the preparation of a hydrazide derivative according to claim 1, comprising the step of a reductive amination of a hydrazide of Formula II with a compound of Formula III in presence of a reducing agent:

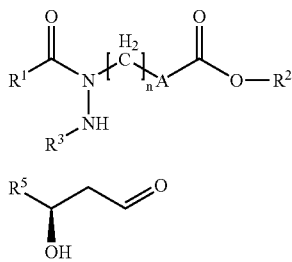
(II)

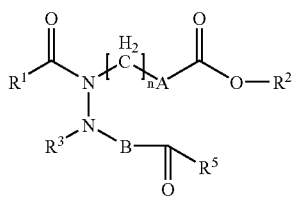
(III)

wherein A, $R^1$, $R^2$, $R^3$ and n are as defined above; $R^5$ is —$CH_2$—$R^6$ wherein $R^6$ is selected from $C_1$-$C_5$ alkyl, $C_2$-$C_5$ alkenyl, $C_2$-$C_5$ alkynyl, $C_1$-$C_5$ heteroalkyl, $C_1$-$C_5$ alkyl $C_1$-$C_5$ alkyl, aryl $C_1$-$C_5$ alkyl and heteroaryl $C_1$-$C_5$ alkyl.

20. A process for the preparation of a hydrazide derivative according to claim 1, comprising the step of a reduction of a compound of Formula IV:

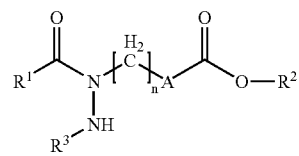
(IV)

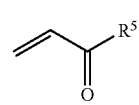

wherein A, B, $R^1$, $R^2$, $R^3$, $R^5$ and n are defined above.

21. The process according to claim 20, further comprising the step of an addition of compound of Formula V to a compound of Formula II through a Michael addition [to obtain a compound of formula IV:]

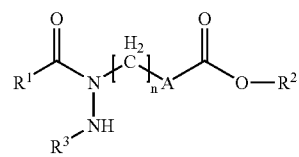
(II)

(V)

wherein A, B, $R^1$, $R^2$, $R^3$ and $R^5$ are as defined above; $R^4$ is H.

22. The process according to claim 19, further comprising the step of saponification of the resulting compound of Formula I, wherein $R^1$ is not H into a compound of Formula I, and wherein $R^2$ is H.

23. The process according to claim 19, wherein A is phenyl.

24. A compound of Formula II:

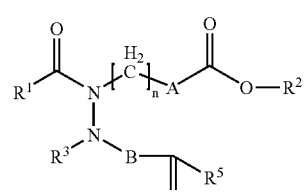
(II)

as well as its geometrical isomers, its optically active forms as enantiomers, diastereomers and mixtures of these, as well as salts thereof, wherein A, $R^1$, $R^2$, $R^3$ and n are as defined above.

25. A compound of Formula IV:

(IV)

as well as its geometrical isomers, its optically active forms as enantiomers, diastereomers and mixtures of these, as well as salts thereof, wherein A, $R^1$, $R^2$, $R^3$, $R^5$ and n are as defined above.

* * * * *